United States Patent
Brockunier et al.

[11] Patent Number: 6,043,253
[45] Date of Patent: Mar. 28, 2000

[54] FUSED PIPERIDINE SUBSTITUTED ARYLSULFONAMIDES AS β3-AGONISTS

[75] Inventors: Linda Brockunier, Orange; Ann E. Weber; Emma R. Parmee, both of Scotch Plains, all of N.J.

[73] Assignee: Merck & Co., Inc., Rahway, N.J.

[21] Appl. No.: 09/257,707

[22] Filed: Feb. 25, 1999

Related U.S. Application Data

[60] Provisional application No. 60/076,580, Mar. 3, 1998.

[51] Int. Cl.$^7$ .......................... C07D 217/00; A61K 31/47
[52] U.S. Cl. ............................ 514/307; 546/149
[58] Field of Search ............................ 546/149; 514/307

[56] References Cited

U.S. PATENT DOCUMENTS

| | | | |
|---|---|---|---|
| 4,999,377 | 3/1991 | Caulkett et al. | 514/507 |
| 5,017,619 | 5/1991 | Alig et al. | 514/653 |
| 5,153,210 | 10/1992 | Ainsworth et al. | 514/369 |
| 5,294,621 | 3/1994 | Russell | 514/301 |
| 5,451,677 | 9/1995 | Fisher et al. | 546/138 |

FOREIGN PATENT DOCUMENTS

| | | |
|---|---|---|
| 0 427 480 A1 | 11/1990 | European Pat. Off. . |
| 0 455 006 A2 | 4/1991 | European Pat. Off. . |
| WO 93/17682 | 9/1993 | WIPO . |
| WO 95/29159 | 11/1995 | WIPO . |
| WO 99/16752 | 4/1999 | WIPO . |

OTHER PUBLICATIONS

Konar, AA et al, Eur. J. Pharmacol., 1996, 305:63–71.
Konar, AA et al, American Society for Pharmacology and Experimental Therapeutics, Mar. 1997 Meeting Abstract No. 142.
He, et al. J. of China Pharm. University, vol. 29, No. 3, pp. 157–160, 1998.

*Primary Examiner*—Zinna Northington Davis
*Attorney, Agent, or Firm*—Mollie M. Yang; David L. Rose

[57] ABSTRACT

Fused piperidine substituted arylsulfonamides are $\beta_3$ adrenergic receptor agonists with very little $\beta_1$ and $\beta_2$ adrenergic receptor activity and as such the compounds are capable of increasing lipolysis and energy expenditure in cells. The compounds thus have potent activity in the treatment of Type II diabetes and obesity. The compounds can also be used to lower triglyceride levels and cholesterol levels or raise high density lipoprotein levels or to decrease gut motility. In addition, the compounds can be used to reduced neurogenic inflammation or as antidepressant agents. Compositions and methods for the use of the compounds in the treatment of diabetes and obesity and for lowering triglyceride levels and cholesterol levels or raising high density lipoprotein levels or for decreasing gut motility are also disclosed.

17 Claims, No Drawings

FUSED PIPERIDINE SUBSTITUTED ARYLSULFONAMIDES AS β3-AGONISTS

CROSS REFERENCE TO RELATED APPLICATIONS

This application is based on and claims priority from U.S. provisional application No. 60/076,580 filed Mar. 3, 1998, which is hereby incorporated by reference in its entirety.

SUMMARY OF THE INVENTION

The instant invention is concerned with fused piperidine substituted arylsulfonamides which are useful as antiobesity and antidiabetic compounds. Thus, it is an object of this invention to describe such compounds. It is a further object to describe the specific preferred stereoisomers of the substituted sulfonamides. A still further object is to describe processes for the preparation of such compounds. Another object is to describe methods and compositions which use the compounds as the active ingredient thereof. Further objects will become apparent from reading the following description.

BACKGROUND OF THE INVENTION

β-Adrenoceptors have been subclassified as $\beta_1$ and $\beta_2$ since 1967. Increased heart rate is the primary consequence of $\beta_1$-receptor stimulation, while bronchodilation and smooth muscle relaxation typically result from $\beta_2$ stimulation. Adipocyte lipolysis was initially thought to be solely a $\beta_1$-mediated process. However, more recent results indicate that the receptor mediating lipolysis is atypical in nature. These atypical receptors, later called $\beta_3$-adrenoceptors, are found on the cell surface of both white and brown adipocytes where their stimulation promotes both lipolysis (breakdown of fat) and energy expenditure.

Early developments in this area produced compounds with greater agonist activity for the stimulation of lipolysis ($\beta_3$ activity) than for stimulation of atrial rate ($\beta_1$) and tracheal relaxation ($\beta_2$). These early developments disclosed in Ainsworth et al., U.S. Pat. Nos. 4,478,849 and 4,396,627, were derivatives of phenylethanolamines.

Such selectivity for $\beta_3$-adrenoceptors could make compounds of this type potentially useful as antiobesity agents. In addition, these compounds have been reported to show antihyperglycemic effects in animal models of non-insulin-dependent diabetes mellitus.

A major drawback in treatment of chronic diseases with $\beta_3$ agonists is the potential for stimulation of other β-receptors and subsequent side effects. The most likely of these include muscle tremor ($\beta_2$) and increased heart rate ($\beta_1$). Although these phenylethanolamine derivatives do possess some $\beta_3$ selectivity, side effects of this type have been observed in human volunteers. It is reasonable to expect that these side effects resulted from partial $\beta_1$ and/or $\beta_2$ agonism.

More recent developments in this area are disclosed in Ainsworth et al., U.S. Pat. No. 5,153,210, Caulkett et al., U.S. Pat. No. 4,999,377, Alig et al., U.S. Pat. No. 5,017,619, Lecount et al., European Patent 427480 and Bloom et al., European Patent 455006.

Even though these more recent developments purport to describe compounds with greater $\beta_3$ selectivity over the $\beta_1$ and $\beta_2$ activities, this selectivity was determined using rodents, in particular, rats as the test animal. Because even the most highly selective compounds, as determined by these assays, still show signs of side effects due to residual $\beta_1$ and $\beta_2$ agonist activity when the compounds are tested in humans, it has become apparent that the rodent is not a good model for predicting human $\beta_3$ selectivity.

Recently, assays have been developed which more accurately predict the effects that can be expected in humans. These assays utilize cloned human $\beta_3$ receptors which have been expressed in Chinese hamster ovary cells. See Emorine et al, Science, 1989, 245:1118–1121; and Liggett, Mol. Pharmacol., 1992, 42:634–637; and Grannemann et al., Mol. Pharmacol., 1992, 42: 964–970. The agonist and antagonist effects of the various compounds on the cultivated cells provide an indication of the antiobesity and antidiabetic effects of the compounds in humans.

U.S. Pat. No. 5,451,677 discloses selective β3 agonists of the formula:

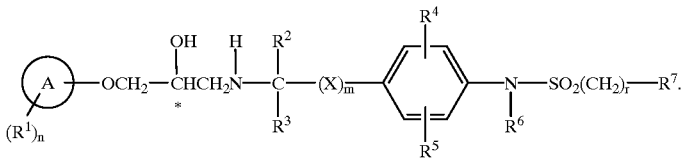

PCT Application WO95/29159 published Nov. 2, 1995 discloses selective β3 agonists of the formula

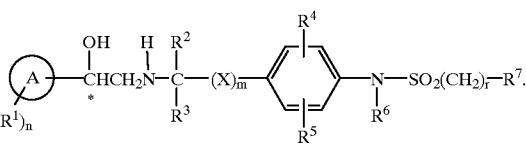

The effect of trimetoquinol and analogs thereof at the β3-adrenoceptor has been studied and potential selective β3-agonists have been reported (see e.g. Konkar, AA et al, Eur. J. Pharmacol., 1996, 305:63–71 and Konkar, AA et al, American Society for Pharmacology and Experimental Therapeutics, March 1997 Meeting, Abstract No. 142).

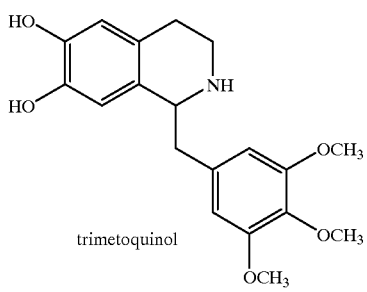

trimetoquinol

PCT Published Application WO93/17682 discloses angiotensin II receptor antagonists having the general formula:

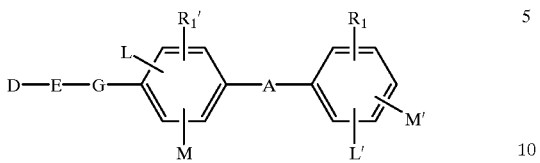

wherein D is a bicyclic heterocyle, E-G may be ethylene or methyleneoxy, A may be a bond, and R1 may be alkyl- or halo-substituted alkylsulfonamide.

DETAILED DESCRIPTION OF THE INVENTION

The present invention provides compounds of the formula I:

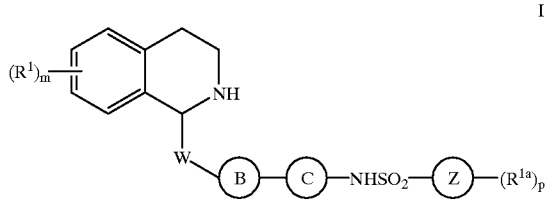

wherein m and p are independently 0 to 5;

W is (1) a bond,
(2) $C_1$–$C_5$ alkylene,
(3) $C_1$–$C_5$ alkylene wherein said alkylene contains an oxygen, with the proviso that the oxygen is not directly attached to the piperidine ring;

B is (1) phenyl,
(2) naphthyl,
(3) a 5 or 6-membered heterocyclic ring with from 1 to 4 heteroatoms selected from oxygen, sulfur and nitrogen,
(4) a benzene ring fused to a $C_5$–$C_{10}$ carbocyclic ring,
(5) a benzene ring fused to a 5 or 6-membered heterocyclic ring with from 1 to 4 heteroatoms selected from oxygen, sulfur and nitrogen,
(6) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or
(7) a 5 or 6-membered heterocyclic ring with from 1 to 4 heteroatoms selected from oxygen, sulfur and nitrogen fused to a $C_5$–$C_{10}$ carbocyclic ring;

C is (1) B, or
(2) a bond;

Z is (1) B,
(2) $C_1$–$C_{10}$ alkyl optionally substituted with B-$(R^{1a})_p$, with the proviso that when B and C are both phenyl, Z is B or $C_1$–$C_{10}$ alkyl substituted with B-$(R^{1a})_p$;

$R^1$ and $R^{1a}$ are independently
(1) $C_1$–$C_{10}$ alkyl optionally substituted with up to 5 groups selected from
(a) Q'$CO_2R^2$,
(b) halogen,
(c) cyano,
(d) $QR^2$,
(e) $C_3$–$C_8$ cycloalkyl,
(f) B optionally substituted with up to 5 groups selected from halogen, $R^2$, $QR^2$, oxo, and $CO_2R^2$;
(g) Q'$COR^3$,
(h) $S(O)_nNR^2R^2$, where n is 0 to 2, and
(i) $NR^2SO_2R^3$;
(2) $C_3$–$C_8$ cycloalkyl,
(3) oxo,
(4) halogen,
(5) cyano,
(6) $QR^2$,
(7) $S(O)_nNR^2R^2$, where n is 0 to 2,
(8) Q'$COR^3$,
(9) $NR^2SO_2R^3$,
(10) Q'$CO_2R^2$, or
(11) B optionally substituted with up to 5 groups independently selected from
(a) $R^2$,
(b) $QR^2$,
(c) halogen, and
(d) oxo;

$R^2$ is (1) hydrogen,
(2) $C_1$–$C_{10}$ alkyl optionally substituted with up to 5 groups selected from
(a) hydroxy,
(b) halogen,
(c) $CO_2R^4$,
(d) $S(O)_n$-$C_1$–$C_{10}$ alkyl, where n is 0 to 2,
(e) $C_3$–$C_8$ cycloalkyl,
(f) $C_1$–$C_{10}$ alkoxy, and
(g) B optionally substituted with up to 5 groups selected from halogen, trifluoromethyl, trifluoromethoxy, cyano, $C_1$–$C_{10}$ akl and $C_1$–$C_{10}$ alkoxy,
(3) $C_3$–$C_8$ cycloalkyl, or
(4) B optionally substituted with up to 5 groups selected from
(a) halogen,
(b) nitro,
(c) oxo,
(d) $NR^4R^4$,
(e) $C_1$–$C_{10}$ alkoxy, optionally substituted with up to 5 halogens,
(f) $S(O)_n$—$C_1$–$C_{10}$ alkyl where n is 0 to 2,
(g) $C_1$–$C_{10}$ alkyl optionally substituted with up to 5 groups selected from hydroxy, halogen, trifluoromethyl, cyano, $CO_2R^4$, $C_3$–$C_8$ cycloalkyl, $S(O)_n$-$R^5$ where n is 0 to 2, $OR^5$, and $NR^4R^4$,
(h) hydroxy, and
(i) cyano;

$R^3$ is (1) $R^2$ or
(2) $NR^2R^2$;

$R^4$ is (1) H, or
(2) $C_1$–$C_{10}$ alkyl;

$R^5$ is (1) B optionally substituted with up to 5 groups selected from halogen, trifluoromethyl, trifluoromethoxy, cyano, $C_1$–$C_{10}$ alkyl and $C_1$–$C_{10}$ alkoxy, or
(2) $C_1$–$C_{10}$ alkyl;

Q is (1) $N(R^2)$,
(2) O or
(3) $S(O)_n$, and n is 0 to 2;

Q' is (1) $N(R^2)$,
(2) O or
(3) a bond; or a pharmaceutically acceptable salt thereof.

In one subset of compounds of formula I B is phenyl or naphthyl.

In another subset of compounds of formula I C is a bond or phenyl.

In another subset of compounds of formula I Z is phenyl or a benzene ring fused to a 5- or 6-membered heterocyclic ring with from 1 to 4 heteroatoms selected from oxygen, sulfur and nitrogen.

In a preferred embodiment of compounds of formula I

W is (1) $C_1$–$C_5$ alkylene or
  (2) $C_1$–$C_5$ alkyleneoxy wherein the oxygen is attached to B;

B is (1) phenyl or
  (2) naphthyl;

C is (1) a bond or
  (2) phenyl;

Z is (1) phenyl or
  (2) a benzene ring fused to a 5- or 6-membered heterocyclic ring with from 1 to 4 heteroatoms selected from oxygen, sulfur and nitrogen;

$R^1$ is (1) $C_1$–$C_{10}$ alkyl optionally substituted with up to 5 groups selected from
  (a) $Q'CO_2R^2$,
  (b) halogen,
  (c) cyano,
  (d) $QR^2$,
  (e) $Q'COR^3$,
  (f) $S(O)_nNR^2R^2$, where n is 0 to 2, and
  (g) $NR^2SO_2R^3$;
(2) halogen,
(3) cyano,
(4) $QR^2$,
(5) $S(O)_nNR^2R^2$, where n is 0 to 2,
(6) $Q'COR^3$,
(7) $NR^2SO_2R^3$, or
(8) $Q'CO_2R^2$; and m, p, Q, Q', $R^2$ and $R^3$ are as defined under formula I.

More preferred compounds are those of formula Ia wherein
$R^1$ is (1) halogen
  (2) hydroxy
$R^{1a}$ is (1) $Q'COR^3$
  (2) a 5 or 6-membered heterocyclic ring with from 1 to 4 heteroatoms selected from oxygen, sulfur and nitrogen, optionally substituted with up to 5 groups independently selected from
    (a) $R^2$,
    (b) $QR^2$,
    (c) halogen,
    (d) cyano, and
    (e) oxo;

$R^2$ is (1) phenyl, optionally substituted with up to 5 groups selected from
  (a) halogen,
  (b) cyano,
  (c) $C_1$–$C_{10}$ alkoxy, optionally substituted with up to 5 halogens,
  (d) $C_1$–$C_{10}$ alkyl optionally substituted with up to 5 halogens,
(2) $C_1$–$C_{10}$ alkyl optionally substituted with up to 5 groups selected from
  (a) hydroxy,
  (b) halogen,
  (c) $CO_2R^4$,
  (d) $S(O)_n$—$C_1$–$C_{10}$ alkyl, where n is 0 to 2,
  (e) $C_3$–$C_8$ cycloalkyl,
  (f) $C_1$–$C_{10}$ alkoxy, and
  (g) B, where B is as defined under Formula I, optionally substituted with up to 5 groups selected from halogen, trifluoromethyl, trifluoromethoxy, cyano, $C_1$–$C_{10}$ alkyl and $C_1$–$C_{10}$ alkoxy;

$R^3$ is $NR^2R^2$; and m, p, Q, Q', and $R^4$ are as defined under Formula I.

Within compounds of Formula Ia, the more preferred are those wherein $R^1$ is hydroxy and m is 1 or 2; $R^{1a}$ is $Q'COR^3$ or a 5 or 6-membered heterocyclic ring with from 1 to 4 heteroatoms selected from oxygen, sulfur and nitrogen, optionally substituted with $R^2$, and p is 1.

Representative compounds of Formula I include:
1. N-[4-[(6,7-dihydroxy-1,2,3,4-tetrahydro-1-isoquinolinyl) methyl]phenyl]-4-[[(hexylamino)carbonyl]amino] benzenesulfonamide, trifluoroacetate;
2. N-[4-[(6,7-dihydroxy-1,2,3,4-tetrahydro-1-isoquinolinyl) methyl]phenyl]-1-[(4-octyl)-2-thiazolyl]-5-indolinesulfonamide, trifluoroacetate;
3. N-[4-[(6,7-dihydroxy-1,2,3,4-tetrahydro-1-isoquinolinyl) methyl]phenyl]-4-(3-octyl-2-imidazolidinon-1-yl) benzenesulfonamide, trifluoroacetate;
4. N-[4-[(6,7-dihydroxy-1,2,3,4-tetrahydro-1-isoquinolinyl) methyl]phenyl]-4-iodobenzenesulfonamide, trifluoroacetate;

Ia

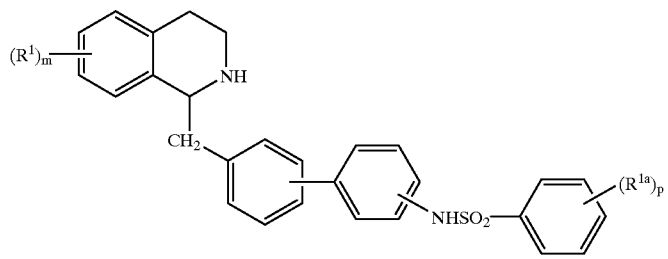

5. N-[4-[(6,7-dihydroxy-1,2,3,4-tetrahydro-1-isoquinolinyl) methyl]phenyl]-4-[6-[4-(trifluoromethyl)phenyl]pyrazin-2-yl]benzenesulfonamide, trifluoroacetate;
6. N-[4'-[(6,7-dihydroxy-1,2,3,4-tetrahydro-1-isoquinolinyl)methyl][1,1'-biphenyl]-3-yl]-4-[[(hexylamino)carbonyl]amino]benzenesulfonamide, trifluoroacetate;
7. N-[3'-[(6,7-dihydroxy-1,2,3,4-tetrahydro-1-isoquinolinyl)methyl][1,1'-biphenyl]-4-yl]-4-[[(hexylamino)carbonyl]amino]benzenesulfonamide, trifluoroacetate;

8. N-[4'-[(6,7-dihydroxy-1,2,3,4-tetrahydro-1-isoquinolinyl)methyl][1,1'-biphenyl]-4-yl]-4-[[(hexylamino)carbonyl]amino]benzenesulfonamide, trifluoroacetate;
9. N-[4'-[(6,7-dihydroxy-1,2,3,4-tetrahydro-1-isoquinolinyl)methyl][1,1'-biphenyl]-4-yl]-4-iodobenzenesulfonamide;
10. N-[4'-[(6,7-dihydroxy-1,2,3,4-tetrahydro-1-isoquinolinyl)methyl][1,1'-biphenyl]-4-yl]-4-[4-[4-(trifluoromethyl) phenyl]thiazol-2-yl] benzenesulfonamide;
11. N-[4'-[(6,7-dihydroxy-1,2,3,4-tetrahydro-1-isoquinolinyl)methyl][1,1'-biphenyl]-4-yl]-3-isoquinolinesulfonamide;
12. N-[4'-[(6,7-dihydroxy-1,2,3,4-tetrahydro-1-isoquinolinyl)methyl][1,1'-biphenyl]-4-yl]-4-(trifluoromethoxy)benzenesulfonamide;
13. N-[4'-[(6,7-dihydroxy-1,2,3,4-tetrahydro-1-isoquinolinyl)methyl][1,1'-biphenyl]-4-yl]-methanesulfonamide;
14. N-[4'-[(6,7-dihydroxy-1,2,3,4-tetrahydro-1-isoquinolinyl)methoxy][1,1'-biphenyl]-4-yl]-4-[[(hexylamino)carbonyl]amino]benzenesulfonamide, trifluoroacetate;
15. N-[4'-[(6,7-dihydroxy-1,2,3,4-tetrahydro-1-isoquinolinyl)methoxy][1,1'-biphenyl]-4-yl]-4-iodobenzenesulfonamide, trifluoroacetate;
16. N-[6-[(6,7-dihydroxy-1,2,3,4-tetrahydro-1-isoquinolinyl)methoxyl naphth-2-yl]-4-[[(hexylamino)carbonyl]amino]benzenesulfonamide, trifluoroacetate;
17. N-[6-[(6,7-dihydroxy-1,2,3,4-tetrahydro-1-isoquinolinyl)methoxy]naphth-2-yl]-4-iodobenzenesulfonamide, trifluoroacetate;
18. N-[4'-[(7-hydroxy-1,2,3,4-tetrahydro-1-isoquinolinyl)methyl][1,1'-biphenyl]-4-yl]-4-[[(hexylamino)carbonyl]amino]benzenesulfonamide, trifluoroacetate;
19. N-[4'-[(7-hydroxy-1,2,3,4-tetrahydro-1-isoquinolinyl)methyl][1,1'-biphenyl]-4-yl]-4-iodobenzenesulfonamide, trifluoroacetate.

Throughout the instant application, the following terms have the indicated meanings:

"Alkylene" means —$(CH_2)_p$— where p is the designated carbon number; one or two of the hydrogen may be optionally replaced by methyl or halogen.

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

The term "carbocyclic ring" is intended to include both aromatic and nonaromatic rings containing only carbon atoms. Thus, a benzene ring fused to a $C_5$–$C_{10}$ carbocyclic ring, includes naphthyl, tetrahydronaphthyl, indenyl and indenyl. A 5 or 6-membered heterocyclic ring with from 1 to 4 heteroatoms selected from oxygen, sulfur and nitrogen fused to a $C_5$–$C_{10}$ carbocyclic ring includes benzene fused to a heterocyclic ring as well as a non-aromatic carbocyclic ring fused to a heterocyclic ring. The carbocyclic ring preferably is $C_5$–$C_7$.

A 5 and 6-membered heterocyclic ring, whether isolated or as a part of a fused ring system, is intended to include aromatic and non-aromatic heterocycles; and where the heterocycle is part of a fused ring, at least one of the rings is aromatic. Examples of a 5 or 6-membered ring include pyridyl, pyrimidinyl, pyrrolyl, furyl, thienyl, imidazolyl, thiazolyl, thiadiazolyl, tetrazolyl, oxadiazolyl, oxazolyl, imidazolidinyl, pyrazolyl, isoxazolyl. Examples of a benzene ring fused to a 5 or 6-membered heterocyclic ring include benzothiadiazolyl, indolyl, indolinyl, benzodioxolyl, benzodioxanyl, benzothiophenyl, benzofuranyl, benzimidazolyl, benzoxazinyl, benzisoxazolyl, benzothiazolyl, 2,3-dihydrobenzofuranyl, quinolinyl, benzotriazolyl, benzoxazolyl, 1,2,3,4-tetrahydroisoquinolinyl, 1,2,3,4-tetrahydroquinolinyl. Examples of a 5 or 6-membered heterocyclic ring fused to a 5 or 6-membered heterocyclic ring include purinyl, furopyridine and thienopyridine. Examples of a 5 or 6-membered heterocyclic ring fused to a non-aromatic carbocyclic ring include tetrahydrobenzothiazolyl, 5,6,7,8-tetrahydroquinolinyl, 2,3-cyclopentenopyridyl, 4,5,6,7-tetrahydroindolyl, 5,6,7,8-tetrahydroisoquinolyl, 5,6,7,8-tetrahydroquinoxalinyl.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Throughout the instant application, when reference is made to "compounds of Formula I" it is meant to include, unless otherwise specified, pharmaceutically acceptable salts and prodrugs thereof. Prodrugs are derivatives of compounds of Formula I that are transformed in vivo to the active drug molecule; prodrugs include derivatives of free hydroxy, amino or carboxylic groups such as esters, ethers, amides, carbonates, carbamates, and N-alkyl derivatives. Specific examples of prodrugs of compounds of Formula I include derivation of the secondary amine such as N-alkylation (methyl, ethyl, isopropyl and 2-methoxyethyl), and N-acylation (1-pyrrolidinylacetyl, 4-morpholinylacetyl, (1-acetoxy)ethoxycarbonyl, and dimethylaminoacetyl). Prodrugs of the above-described types may be readily prepared from compounds of Formula I using methods well known to persons skilled in the art.

Certain of the above defined terms may occur more than once in the above formula and upon such occurrence each term shall be defined independently of the other; thus for example, $NR^2R^2$ may represent $NH_2$, $NHCH_3$, $N(CH_3)CH_2CH_3$, and the like.

The following are abbreviations used throughout the applications:

| | |
|---|---|
| Bn | benzyl |
| BOC (boc) | t-butyloxycarbonyl |
| DMF | dimethylformamide |
| EDC | 1-(3-dimethylaminopropyl)3-ethylcarbodiimide HCl |
| n-Hex | n-hexyl |
| Me | methyl |

-continued

| | |
|---|---|
| MHz | megahertz |
| NMR | nuclear magnetic resonance |
| Ph | phenyl |
| prep. | prepared |
| Tf | trifluoromethanesulfonyl |
| TFA | trifluoroacetic acid |
| THF | tetrahydrofuran |
| TLC | thin-layer chromatography |

The compounds (I) of the present invention can be prepared as described in the following schemes. In the following schemes the notation

represents a benzene ring. As illustrated in Scheme 1, compounds (I) may be prepared using the Bishler-Napieralski reaction (T. Kametani and K Fukumoto in "The Chemistry of Heterocyclic Compounds", Vol. 38, Pt. 1, pp. 142–160, 1981). Amine 1 is coupled to acid 2 using a coupling reagent, conveniently EDC in DMF, to provide amide 3. Coupling with the appropriate sulfonyl chloride 4 is readily accomplished, for example, in dichloromethane with pyridine, to provide sulfonamide 5. Bishler-Napieralski cyclization of 5 is effected with, for example, phosphorous oxychloride, zinc chloride or phosphorous pentachloride. Reduction of the intermediate imine, for example by treatment with sodium borohydride, provides the desired compound (I).

Substituted ethylamines 1 and acids 2 are commercially available, known in the literature, or readily prepared by methods known to those skilled in the art. Sulfonyl chlorides 4, many of which are commercially available, can also be readily prepared by a number of methods familiar to those skilled in the art. One suitable method involves the addition of an organolithium reagent or a Grignard reagent to sulfrryl chloride following the procedure of S. N. Bhattacharya, et. al., J. Chem. Soc. (C), 1265–1267 (1969). Another convenient method involves the treatment of a thiol with sulfuryl chloride and a metal nitrate according to the procedure of Y. J. Park, et. al., Chemistry Letters, 1483–1486 (1992). Sulfonic acids are also conveniently converted to the corresponding sulfonyl chloride by treatment with $PCl_5$, $PCl_3$ or $SOCl_2$ (J. March, *Advanced Organic Chemistry*, 4th Ed., John Wiley and Sons, New York: 1992, p1297 and references cited therein). Aromatic and heteroaromatic compounds may be chlorosulfonylated directly by treatment with Vilsmeier's reagent or chorosulfonic acid (Organic Synthesis, I, 8).

An alternative route to compounds (I) is shown in Scheme 2. Amine 1 is coupled to acid 6, conveniently with a coupling reagent such as EDC in DMF, to provide amide 7. Bischler-Napieralski cyclization of 7 followed by reduction as described above provides amine 8. Protection of the amine in 8, for example, as its tert-butyl carbamate by treatment with di-tert-butyldicarbonate, followed by reduction of the nitro group, conveniently with hydrazine and Raney nickel, gives amine 9. Coupling with the appropriate sulfonyl chloride 4, for example in dichloromethane with pyridine, followed by removal of the amine protecting group, conveniently in the case of tert-butyl carbonate by treatment with trifluoroacetic acid in dichloromethane, or methanolic hydrogen chloride, or concentrated hydrochloric acid in methanol, provides compound (I).

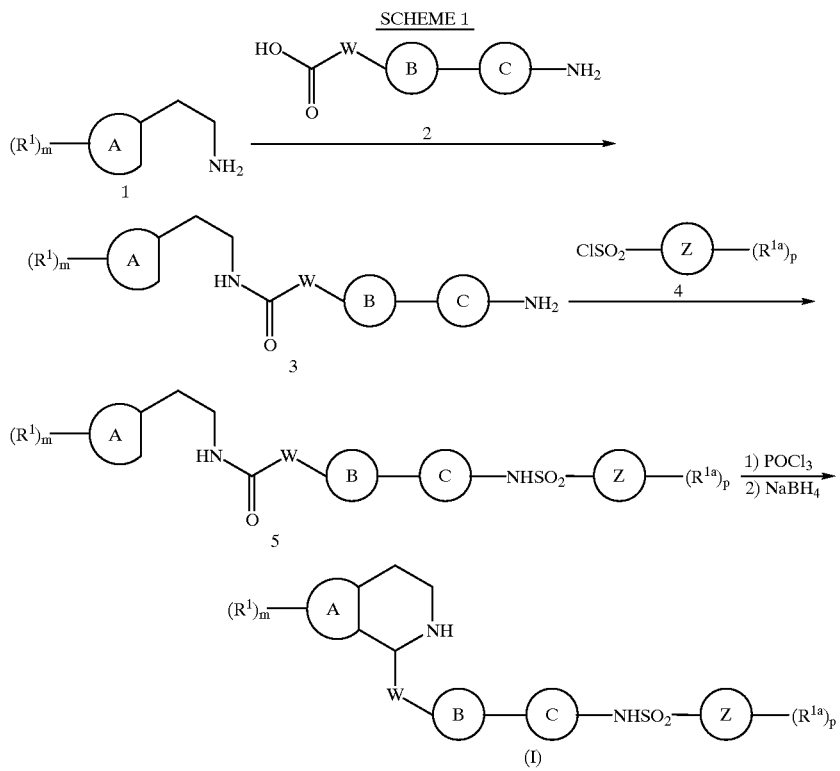

SCHEME 1

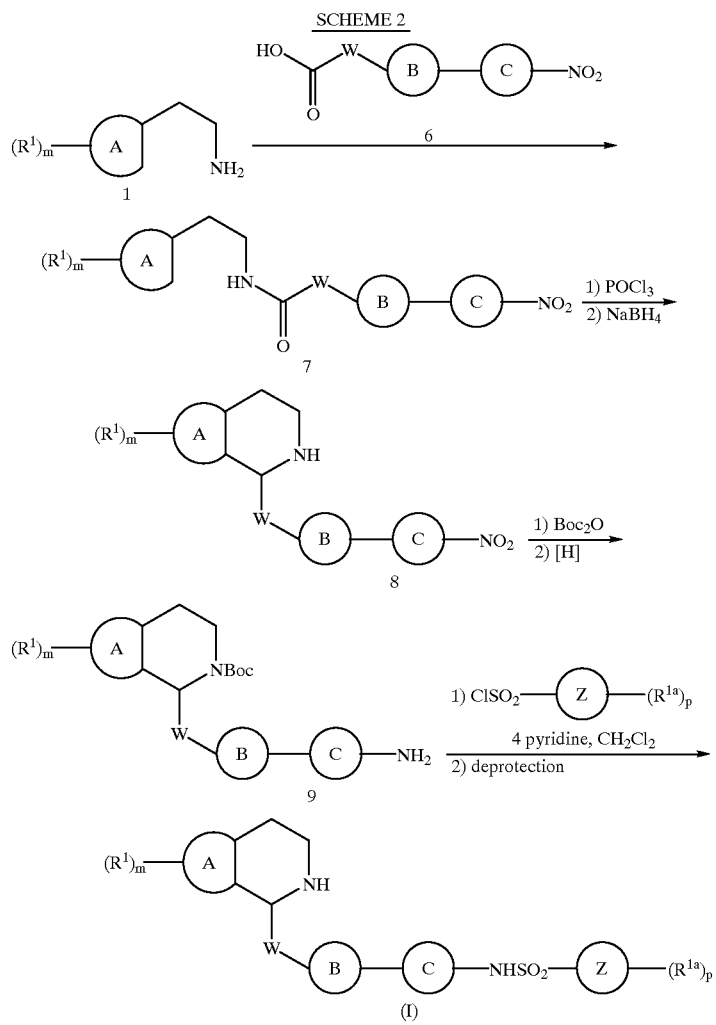

A third route to compound (I) is illustrated in Scheme 3. Amine 1 is coupled, conveniently using a coupling reagent such as EDC in DMF, to acid 10, which contains a halogen group X, for example bromide, to provide amide 11. Bischler-Napieralski cyclization of 11 followed by reduction as described above provides amine 12. Protection of the amine in 12, for example, as its tert-butyl carbamate by treatment with di-tert-butyldicarbonate, gives amine 13. Cross coupling of 13 and sulfonamide 14, which contains an appropriate functional group X', is accomplished conveniently in the presence of a palladium catalyst using Stille conditions (J. K. Stille, *Angew. Chem. Int. Ed. Engl.* 1986, 25, 508–524) when X' is an organostannane derivative, for example tributyltin, or Suzuki conditions (A. Suzuki, *Pure Appl. Chem.* 1991, 63, 419–422) when X' is an organoboron derivative or a boronic acid or ester. Removal of the amine protecting group, conveniently in the case of tert-butyl carbonate by treatment with trifluoroacetic acid in dichloromethane, or methanolic hydrogen chloride, or concentrated hydrochloric acid in methanol, provides compound (I).

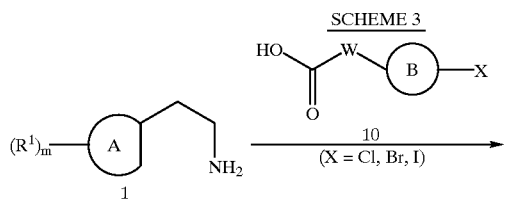

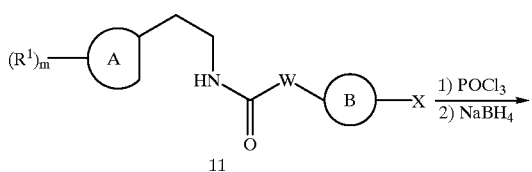

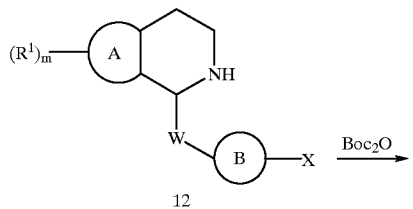

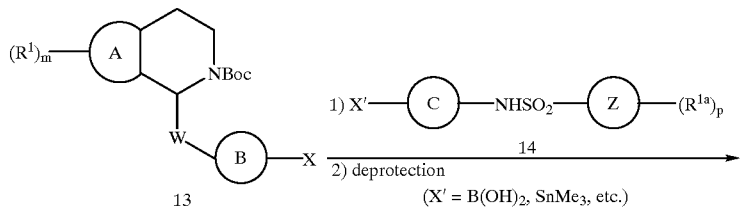

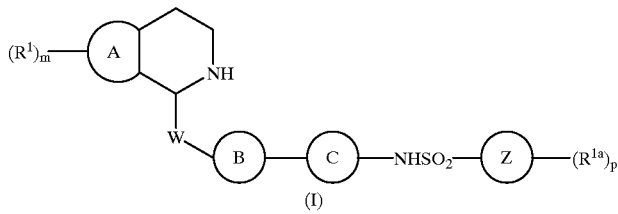

An alternate route to intermediate 9 is illustrated in Scheme 4. Derivative 13, prepared as described for Scheme 3, is cross coupled to amine derivative 15a (X"=NH$_2$) as described above to provide intermediate 9. Alternatively, derivative 13 may be cross coupled with nitro derivative 15b (X"=NO$_2$) followed by reduction of the nitro group, for example with hydrazine and Raney nickel, to give intermediate 9. Derivative 9 may be converted to compound (I) as described in Scheme 2.

SCHEME 4

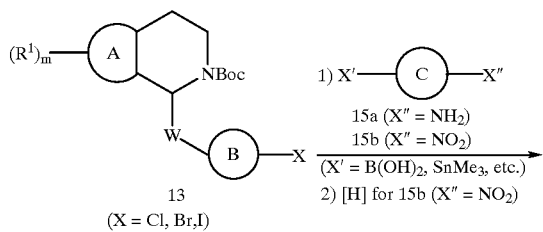

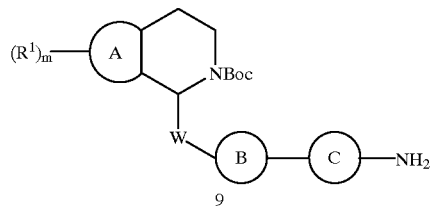

Boron and tin intermediates 14 and 15 are commercially available, known in the literature, or readily prepared by methods known to those skilled in the art. Intermediate 14 may be prepared as shown in Scheme 5. Coupling of amino halide 16 with the appropriate sulfonyl chloride 4 provides sulfonamide 17. This compound is conveniently converted to the boronic ester 14 (X'=B(OR)$_2$) by treatment with the pinacol ester of diboron in the presence of a palladium catalyst such as PdCl$_2$(dppf) and a base such as cesium carbonate or potassium acetate according to the conditions of Ishiyama, et al. *J. Org. Chem.* 1995, 60, 7508–7510. The corresponding tin intermediate 14 (X'=SnMe₃) is available from halide 17 by treatment with hexamethyltin and a palladium catalyst such as palladium tetrakis(triphenylphosphine) (see D. Azarian et al., *J. Organomet. Chem.* 1976,117, $C_{55}$–$C_{57}$).

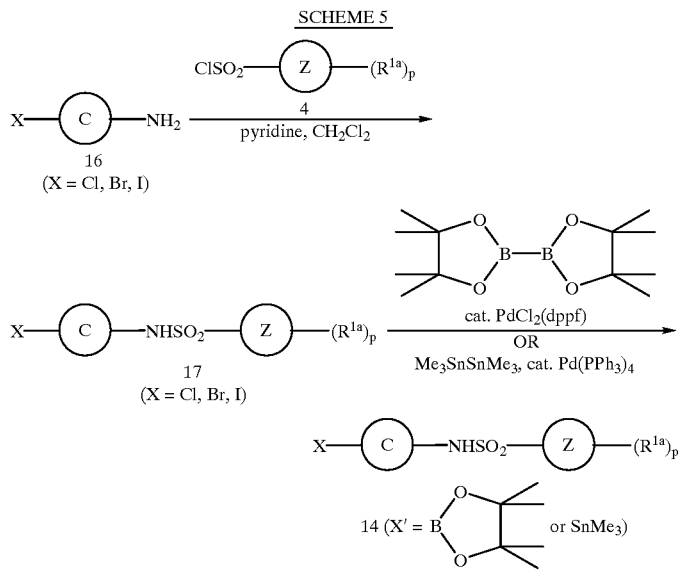

As illustrated in Scheme 6, compounds (I) may be prepared using the Pictet-Spengler reaction (T. Kametani and K Fukumoto in "The Chemistry of Heterocyclic Compounds", Vol. 38, Pt. 1, pp. 170–181, 1981). Amine 1 is treated with aldehyde 18, typically under acidic conditions such as acetic acid in methanol, to give compound (I).

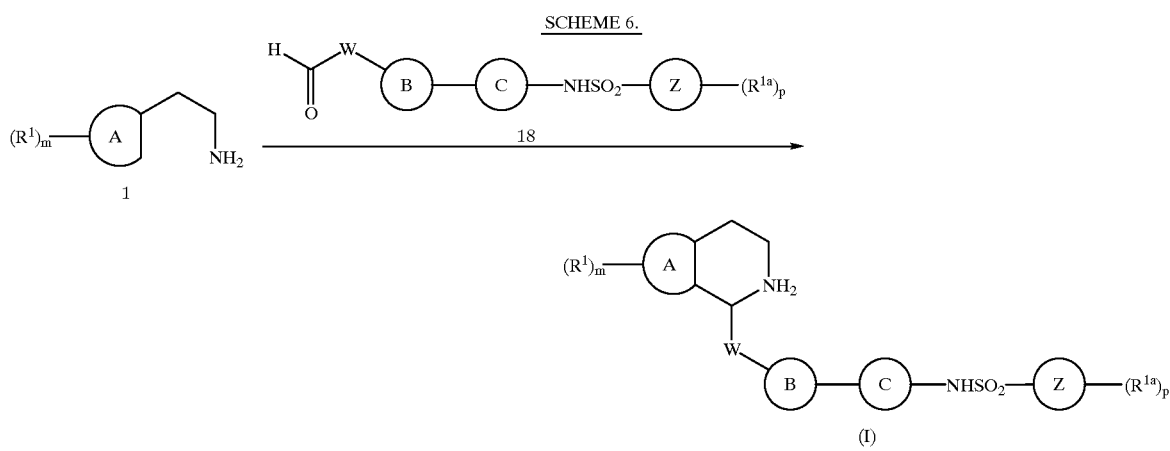

Intermediates 8 and 12 may also be prepared using the Pictet Spengler reaction as illustrated in Schemes 7 and 8, respectively. Treatment of amine 1 with the appropriate aldehyde 19 or 20, conveniently in acetic acid and methanol, provides the desired intermediate 8 (Scheme 7) or 12 (Scheme 8).

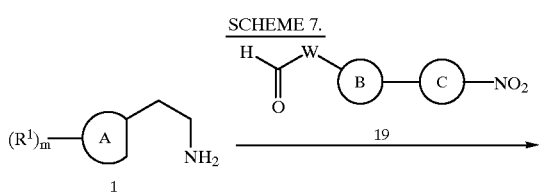

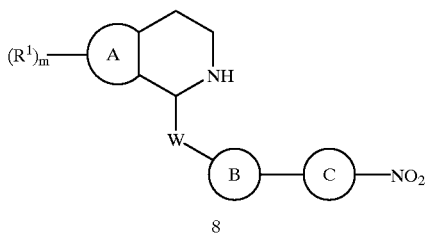

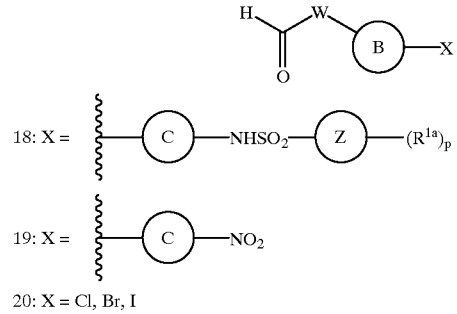

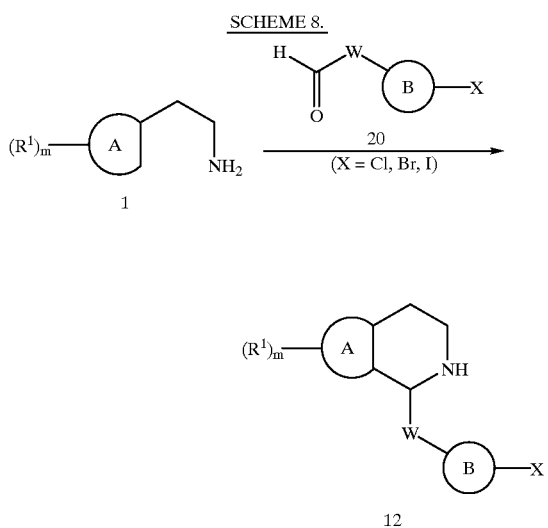

Aldehydes 18, 19, and 20 are commercially available, known in the literature, or may be prepared by methods commonly known to those skilled in the art (For example, see March, "Advanced Organic Chemistry", 4th Ed., Wiley: New York, 1992, 1270–1271, and references therein). One common method involves oxidation of the corresponding alcohols 21, 22, or M (Scheme 9) to give aldehydes 18, 19, or 20, respectively, for example, using the Swern (A. J. Mancuso and D. Swern, *Synthesis* 1981, 165–185) or Dess-Martin (D. B. Dess and J. C. Martin, *J. Amer. Chem. Soc.* 1991, 113, 7277) oxidation reactions.

An alternate route to intermediate 13 where W is methylene and X is trifluoromethanesulfonoxy is illustrated in Scheme 10. Following a procedure outlined in the literature (*Tetrahedron Lett.*, 1998, 39:1721–1724), isoquinoline derivative 24 is treated with an acylating agent such as methyl or ethyl chloroformate followed by a tin reagent 25, for example, trimethyl(4-benyloxyphenyl)tin, to provide the dihydroisoquinoline derivative 26. Reduction with, for example, palladium hydroxide and ammonium formate provides the tetrahydroisoquinoline 27. Under these conditions, the benzyl group on X is also removed to provide the free phenol (X=OH). The ethoxycarbonyl group is removed by treatment under basic conditions such as potassium hydroxide and hydrazine in ethylene glycol. The free nitrogen is then protected, for example, as its tert-butyloxycarbonyl derivative by treatment with di-tert-butyl-dicarbonate. Treatment with triflic anhydride provides intermediate 13, where X is trifluoromethanesulfonoxy. This intermediate is suitable for use in Stille or Suzuki-type couplings as illustrated above in Scheme 3 and Scheme 4.

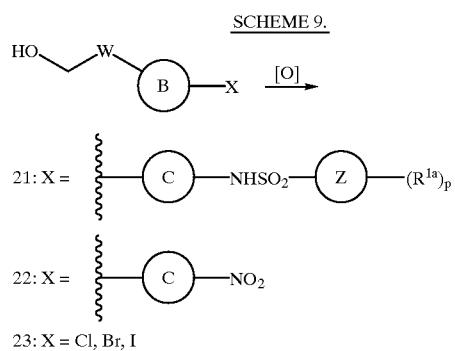

-continued

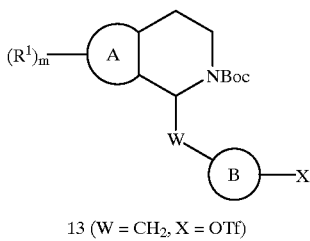

13 (W = CH₂, X = OTf)

Isoquinoline derivatives 24 are commercially available, known in the literature, or readily prepared by methods known to those skilled in the art. One convient method for their preparation is illustrated in Scheme 11. Acid 28 is converted to the corresponding acid chloride 29, for example, by treatment with thionyl chloride or oxalyl chloride. Treatment with a Lewis acid such as aluminum trichloride provides ketone 30. Reduction to alcohol 31 is effected with a reducing agent such as sodium borohydride. Treatment with acid, conveniently aqueous sulfuric acid at elevated temperature, gives the desired indene 32. Indene 32 is converted to isoquinoline 24 as described in the literature (*J. Org. Chem.*, 1980, 45:5312–5315), by treatment with ozone followed by dimethylsulfide, and then ammonium hydroxide.

SCHEME 11.

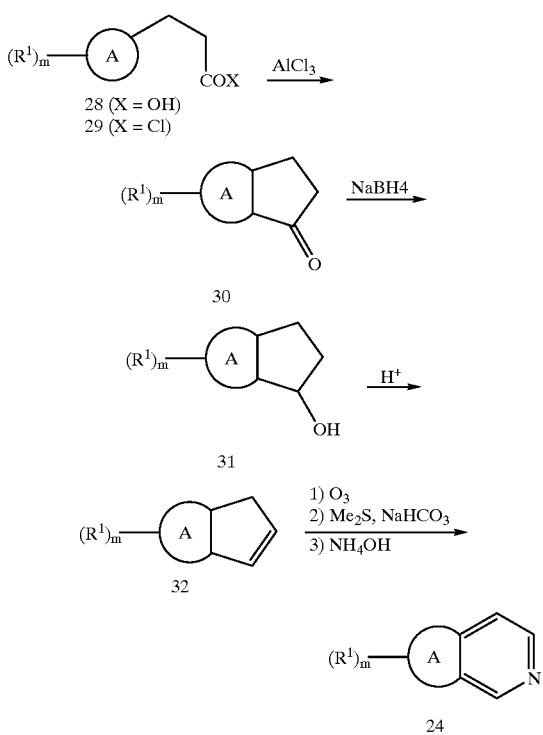

In some cases, the product I from the reactions described in Schemes 1–3 and 6 may be further modified, for example, by the removal of protecting groups or the manipulation of substituents on $R^1$ and/or $R^{1a}$. These manipulations may include, but are not limited to, reduction, oxidation, alkylation, acylation, and hydrolysis reactions, which are commonly known to those skilled in the art.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, fumaric, hydrobromic, hydrochloric, maleic, phosphoric, sulfuric, trifluoroacetic, and tartaric acids.

It will be understood that, as used herein, references to the compounds of Formula I are meant to also include the pharmaceutically acceptable salts.

Utilities

Compounds of the present invention are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound of Formula I. The term "mammal" includes human and non-human animals such as dogs and cats and the like. The diseases, disorders or conditions for which compounds of the present invention are useful in treating or preventing include, but are not limited to, (1) diabetes mellitus, (2) hyperglycemia, (3) obesity, (4) hyperlipidemia, (5) hypertriglyceridemia, (6) hypercholesterolemia, (7) atherosclerosis of coronary, cerebrovascular and peripheral arteries, (8) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (9) neurogenic inflammation of airways, including cough, asthma, (10) depression, (11) prostate diseases such as benign prostate hyperplasia, (12) irritable bowel syndrome and other disorders needing decreased gut motility, (13) diabetic retinopathy, (14) neuropathic bladder dysfunction, and 15) elevated intraocular pressure and glaucoma.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that are used in the treatment/prevention/ suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical unit dosage form containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) insulin sensitizers including (i) PPARγ agonists such as 5 the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide;

(d) α-glucosidase inhibitors (such as acarbose), (e) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (iii) nicotinyl alcohol nicotinic acid or a salt thereof, (iii) proliferator-activater receptor a agonists such as fenofibric acid derivatives (gemfibrozil, clofibrat, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;

(f) PPARδ agonists such as those disclosed in WO97/28149;

(g) antiobesity compounds such as fenfluramine, dexfenfluramine, phentermine, sibutramine, orlistat, and other $\beta_3$ adrenergic receptor agonists;

(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(i) PPARα agonists such as described in WO 97/36579 by Glaxo;

(j) PPARγ antagonists as described in WO97/10813; and (k) serotonin reuptake inhibitors such as fluoxetine and sertraline.

Biological Assays

The following in vitro assays are suitable for screening compounds that have selective β3 agonist activity:

Functional Assay: cAMP production in response to ligand is measured according to Barton et al (1991, Agonist-induced desensitization of D2 dopamine receptors in human Y-79 retinoblastoma cells. Mol. Pharmacol. v3229:650–658) modified as follows. Chinese hamster ovary (CHO) cells, stably transfected with the cloned β-adrenergic receptor ($\beta_1$, $\beta_2$ or $\beta_3$) are harvested after 3 days of subculturing. Harvesting is done with Enzyme-free Dissociation Media (Specialty Media). Cells are counted and distributed in the assay tubes, after being resuspended in Tris buffer (ACC buffer: 75 mM Tris, pH 7.4, 250 mM Sucrose, 12.5 mM $MgCl_2$, 1.5 mM EDTA, 0.2 mM Sodium Metabisulfite, 0.6 mM IBMX) containing an antioxidant and a phosphodiesterase inhibitor. Reaction is initiated by mixing 200,000 cells in 100 μL with 20 μL of a 6× stock of ligand/unknown to be tested. Tubes shake at 275 rpm for 45 min at room temperature. The reaction is stopped by boiling the tubes for 3 min. The cell lysate is diluted 5-fold in 0.1 N HCl and then acetylated by the mixture of 150 μL of acid-diluted sample with 6 μL of acetylation mixture (acetic anhydride/triethylamine, 1:2.5). The cAMP produced in response to the ligand is measured in the lysate by competing against $^{125}$I-cAMP for binding to a $^{125}$I-cAMP-directed antibody using an automated RIA machine (ATTOFLO, Atto Instruments, Baltimore, Md., Brooker et al 1979, Radioimmunoassay of Cyclic AMP and Cyclic GMP. Advances in Cyclic Nucleotide Research. vol 10: 1–32. ). The unknown cAMP level is determined by comparing levels to a standard curve. Alternatively, cAMP is measured using the cAMP SPA kit (code number RPA 556) from Amersham according to the manufacturer's instructions. Samples tested with the latter method do not need to be acetylated.

The non-selective, full agonist β-adrenergic ligand isoproterenol is used at all three receptors to determine maximal stimulation. The human β3 adrenergic receptor (AR) selective ligand (S)-N-[4-[2-[[2-hydroxy-3-(4-hydroxyphenoxy)propyl]amino]ethyl)-phenyl]-4-iodobenzenesulfonamide is used as a control in all assays. Isoproterenol is titrated at a final concentration in the assay of $10^{-10}$ M to $10^{-5}$ M for the β3 AR and $10^{-11}$ M to $10^{-6}$ M for the β1 AR and β2 AR assays. (S)-N-[4-[2-[[2-hydroxy-3-(4-hydroxyphenoxy)propyl]amino]ethyl]phenyl]-4-iodobenzenesulfonamide is titrated at the β3 receptor at concentration of $10^{-11}$ M to $10^{-6}$ M. At the β1 AR the concentrations used are $10^{-8}$ M, $10^{-7}$ M, $3\times10^{-7}$ M, $10^{-6}$ M, $3\times10^{-6}$ M and $10^{-5}$ M. For the β2 AR a single concentration of $10^{-5}$ M is used.

Unknown ligands are initially tested at the β3 AR at a final concentration in the assay of $10^{-7}$ M. Compounds that have an activation at this concentration equal to or greater than 35% of the isoproterenol stimulation are titrated at the β3 AR at concentrations equal to those used to titrate the control (S)-N-[4-[2-[[2-hydroxy-3-(4-hydroxyphenoxy) propyl] amino]ethyl]-phenyl]-4-iodobenzenesulfonamide to determine the $EC_{50}$. The $EC_{50}$ is defined as the concentration of compound that gives 50% activation of its own maximum. Data are analyzed using the Prism program (GraphPan, San Diego, Calif.).

Binding Assay: Compounds are also assayed at the β1 and β2 receptors to determine selectivity. This is done for all compounds using a 6 point binding assay as follows: CHO cells expressing the β1 and the β2 receptors are grown for 3–4 days after splitting. The attached cells are washed with PBS and lysed in 1 mM Tris, pH 7.2 for 10 minutes in ice. The flasks are scraped and the membranes centrifuged at 38,000×g for 15 minutes at 4° C. The membranes are resuspended in TME buffer (75 mM Tris, pH 7.4, 12.5 mM MgCl$_2$, 1.5 mM EDTA) at a concentration of 1 mg protein/ml. Large batches of membranes can be prepared, aliquoted and stored at −70° C. for up to a year without loss of potency. The binding assay is performed by incubating together membranes (20–50 μg of protein), the radiolabelled tracer $^{125}$I-cyanopindolol ($^{125}$I-CYP, 45 pM), and the test compounds at final concentrations ranging from $10^{-10}$ M to $10^{-5}$ M in a final volume of 250 μL of TME buffer. The tubes are incubated for 1 hour with shaking at room temperature and the samples are filtered in an IMSCO 96-well cell harvester. The filters are counted in a Gamma counter and the data are analyzed using a 4 parameter fit routine in RS1 (program developed in house using well documented statistical analysis programs) to determine the IC$_{50}$. The IC$_{50}$ is defined as the concentration of the compound capable of inhibiting 50% of the binding of the radiolabelled tracer ($^{125}$I-CYP). A compound's selectivity for the β3 receptor may be determined by calculating the ratio (IC$_{50}$ β1 AR, β2 AR)/(EC$_{50}$ β3 AR).

The following examples are provided so that the invention might be more fully understood. They should not be construed as limiting the invention in any way.

EXAMPLE 1

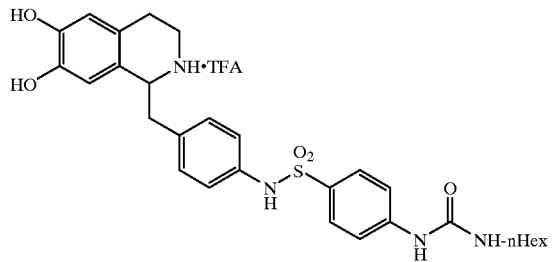

N-[4-[(6,7-Dihydroxy-1,2,3,4-tetrahydro-1-isoquinoinyl) methyl]phenyl]-4-[[(hexlamino)carbonyl]amino] benzenesulfonamide, trifluoroacetate L-821,122

Step A. N-[2-[3,4-Bis(phenylmethoxy)phenyl]ethyl]-4-nitrophenyl-acetamide. To a solution of 667 mg (2 mmol) of 3,4-bis(benzyloxy)-phenethylamine and 0.243 mL (3 mmol) of pyridine in 5 mL of dichloromethane at 0° C. was added a solution of 439 mg (2.2 mmol) of 4-nitrophenylacetyl chloride in 5 mL of dichloromethane. The resultant mixture was stirred at room temperature for 16 h, diluted with dichloromethane, washed sequentially with saturated aqueous sodium bicarbonate solution and brine, dried over magnesium sulfate, and concentrated. The residue was purified by flash chromatography (silica gel, 2% methanol/dichloromethane) to give 600 mg (60%) of the title compound: $^1$H NMR (400 MHz, CDCl$_3$) δ 8.11 (d, 2H, J=8.8 Hz), 7.45– 7.24 (m, 12H), 6.78 (d, 1H, J=8.1 Hz), 6.70 (d, 1H, J=2 Hz), 6.51 (dd, 1H, J=8.1 and 2 Hz), 5.32–5.25 (m, 1H), 5.12 (s, 2H), 5.10 (s, 2H), 3.49 (s, 2H), 3.44–3.39 (m, 2H), 2.64 (t, 2H, J=6.6 Hz).

Step B. 2-[(1,1-Dimethylethoxy)carbonyl]-1-[(4-nitrophenyl)methyl]-6,7-bis(phenylmethoxy)-1,2,3,4-tetrahydroisoquinoline. To a solution of 500 mg (1.01 mmol) of the product from Example 1, Step A in 3 mL of acetonitrile was added 0.75 mL of phosphorus oxychloride. The resultant mixture was stirred at 80° C. for 4 h, concentrated, dissolved in chloroform, and diluted with an ice/water slurry. The biphasic solution was stirred while 2N aqueous sodium hydroxide solution was added until the aqueous phase was basic. The layers were separated and the organic layer was washed sequentially with 2N aqueous sodium hydroxide solution and brine, dried over magnesium sulfate, and concentrated to give a dark red oil. This residue was immediately suspended in 5 mL of ethanol and 96 mg (2.52 mmol) of sodium borohydride was added portionwise. The resultant mixture was stirred for 16 h, concentrated, and partioned between ethyl acetate and water. The layers were separated, the aqueous phase back extracted with ethyl acetate, and the combined organic phases were washed with brine, dried over magnesium sulfate, and concentrated to give 450 mg of product. This was immediately dissolved in 10 mL of THF and 243 mg (1.13 mmol) of di-tert-butyldicarbonate was added. The resultant mixture was stirred for 16 h, diluted with ethyl acetate, washed sequentially with saturated aqueous sodium bicarbonate solution and brine, dried over magnesium sulfate, and concentrated. The residue was purified by radial chromatography (silica gel, 25% ethyl acetate/hexane) to give 387 mg (66%) of the title compound: $^1$H NMR (400 MHz, CD$_3$OD, mixture of rotamers) δ 8.14 (d, 1.2H. J=8.6 Hz), 8.07 (d, 0.8H, J=8.2 Hz), 7.46–7.23 (m, 12H), 6.86 (s, 0.6H), 6.80 (s, 1H), 6.70 (s, 0.4H), 5.21–5.00 (m, 5H), 4.14.0 (m, 0.6H), 3.9–3.8 (m, 0.4H), 3.36–3.05 (m, 3H), 2.8–2.5 (m, 2H), 1.34 (m, 3.6H), 1.18 (m, 5.4H).

Step C. 1-[(4-Aminophenyl)methyl]-2-(1,1-dimethylethoxy)carbonyl]-6,7-bis(phenylmethoxy)-1,2,3,4-tetrahydroisoquinoline. To a solution of 77.9 mg (0.134 mmol) of the product from Example 1, Step B in 2 mL of methanol was added 0.033 mL (0.67 mmol) of hydrazine hydrate, and raney nickel. The resultant mixture was stirred at 60° C. for 10 min, diluted with methanol, filtered through Celite, and concentrated to give 67 mg (91%) of the title compound which was used without further purification: $^1$H NMR (400 MHz, CD$_3$OD, mixture of rotamers) δ 7.45–7.20 (m, 10H), 6.83–6.40 (m, 6H), 5.08–4.95 (m, 5H), 4.01–3.92 (m, 0.67H), 3.80–3.73 (m, 0.33H), 3.28–3.15 (m, 1H), 2.9–2.43 (m, 4H), 1.42 (s, 3H), 1.28 (s, 6H).

Step D. N-[4-[(6,7-Dihydroxy-1,2,3,4-tetrahydro-1-isoquinolinyl)methyl]-phenyl]-4-[[(hexylamino)carbonyl] amino]benzenesulfonamide, trifluoroacetate. To a solution of 25 mg (0.045 mmol) of the product from Example 1, Step C in 2 mL of dichloromethane at 0° C. was added 0.075 mL of pyridine and 23 mg (0.072 mmol) of 4-[[(hexylamino) carbonyl]-amino]benzenesulfonyl chloride. The resultant mixture was stirred at ambient temperature for 16 h, concentrated, and purified by preparative TLC (silica gel, 5% methanol/dichloromethane) to give 34 mg of product. This was taken up in 2 mL methanol and 2 mL of 12 N hydrochloric acid was added. The resultant mixture was stirred at 60° C. for 16 h, concentrated, and purified by preparative TLC (slica gel, 10% methanol/1% ammonium hydroxide/dichloromethane) to give the product, which was further purified by preparative HPLC (Dynamax-60A C-18 column, 65% methanol/35% water/0.35% trifluoroacetic acid) to give 5.7 mg of the title compound: $^1$H NMR (400 MHz, CD$_3$OD) δ 7.65 (d, 2H, J=8 Hz), 7.46 (d, 2H, J=8 Hz), 7.18–7.10 (m, 4H), 6.60 (s, 1H), 6.55 (s, 1H), 4.60–4.56 (m, 1H), 3.40–2.85 (m, 8H), 1.55–1.46 (m, 2H), 1.40–1.27 (m, 6H), 0.91–0.88 (m, 3H).

Following the procedures outlined for Example 1, the compounds listed in Table 1 were prepared.

TABLE 1

| Ex. | R | Selected $^1$H NMR (CD$_3$OD) Data |
|---|---|---|
| 2 | 1-(4-octylthiazol-2-yl)indolin-5-yl, TFA salt L-821,123 | 8.03(d, 1H, J=7Hz), 7.68–7.60(m, 2H), 6.59(s, 1H), 6.53(m, 2H), 4.10 (t, 2H, J=8Hz), 2.64(t, 2H, J=8Hz), 1.75–1.66(m, 2H), 1.40–1.22(m, 10H), 0.91–0.85(m, 3H). |
| 3 | 4-(3-octyl-2-imidazolidinon-1-yl)phenyl, TFA salt L-823,221 | 7.72–7.64(m, 4H), 3.87–3.83(m, 2H), 3.55–3.51(m, 2H), 1.62–1.52(m, 2H), 1.38–1.23(m, 10H), 0.92–0.86(m, 3H). |
| 4 | 4-iodophenyl, TFA salt L-823,421 | 7.88(d, 2H, J=8Hz), 7.52(d, 2H, J=8Hz). |
| 5 | 4-[6-[4-(trifluoromethyl)-phenyl]-pyrazin-2-yl]phenyl, TFA salt L-823,792 | 9.22(s, 1H), 9.18(s,1H), 8.42(d, 2H, J=8.3 Hz), 8.37(d, 2H, J=8.6 Hz), 7.97(d, 2H, J=8.6 Hz), 7.85(d, 2H, J=8.3Hz). |

EXAMPLE 6

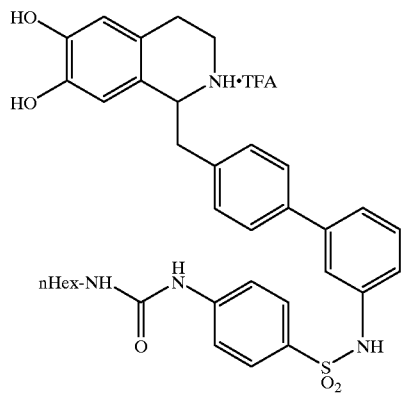

N-4'-[(6,7-Dihydroxy-1,2,3,4-tetrahydro-1-isoruinolinyl) methyl][1,1'-biphenyl]-3-yl]-4-[[(hexylamino)carbonyl] amino]benzenesulfonamide, trifluoroacetate L-825,296

Step A. N-[2-[3,4-Bis(phenylmethoxy)phenyl]ethyl]-4-bromophenyl-acetamide. To a solution of 370 mg (1 mmol) of 3,4-bis(benzyloxy)-phenethylamine hydrochloride and 0.435 mL (2.5 mmol) of N,N-diiso-propylethylamine in 5 mL of DMF was added 215 mg (1 mmol) of 4-bromophenylacetic acid and 210.9 mg (1.1 mmol) of EDC. The resultant mixture was stirred at ambient temperature for 16 h, diluted with water, and extracted with three portions of ethyl acetate. The combined organic phases were washed with brine, dried over magnesium sulfate, and concentrated. The residue was purified by flash chromatography (silica gel, 50% ethyl acetate/hexane) to give 205 mg (45%) of the title compound: $^1$H NMR (400 MHz, CDCl$_3$) δ 7.46–7.25 (m, 12H), 6.98 (d, 2H, J=9 Hz), 6.78 (d, 1H, J=8 Hz), 6.68 (d, 1H, J=2 Hz), 6.45 (dd, 1H, J=2 and 8 Hz), 5.23–5.16 (m, 1H), 5.13 (s, 2H), 5.10 (s, 2H), 3.41–3.32 (m, 4H), 2.60 (t, 2H, J=8 Hz).

Step B. 1-[(4-Bromophenyl)methyl]-2-[(1,1-dimethylethoxy)carbonyl]-6,7-bis(phenylmethoxy)-1,2,3,4-tetrahydroisoquinoline. To a solution of 200 mg (0.437 mmol) of the product from Example 6, Step A in 3.5 mL of acetonitrile was added 0.375 mL of phosphorus oxychloride. The resultant mixture was stirred at 80° C. for 3 h, concentrated, dissolved in chloroform, and washed sequentially with 2 N aqueous sodium hydroxide solution and brine, dried over magnesium sulfate, and concentrated to give a yellow oil. This residue was immediately suspended in 2 mL of ethanol and 41.5 mg (1.09 mmol) of sodium borohydride was added portionwise. The resultant mixture was stirred at ambient temperature for 3 h, concentrated, and partitioned between ethyl acetate and water. The layers were separated, the aqueous phase back extracted with ethyl acetate, and the combined organic phases were washed with brine, dried over magnesium sulfate, and concentrated to give 181 mg of product. This was immediately dissolved in 3 mL of THF and 113 mg (0.524 mmol) of di-t-butyldicarbonate was added. The resultant mixture was stirred at ambient temperature for 3 h, and concentrated. The residue was purified by flash chromatography (silica gel, 15% ethyl acetate/hexane) to give 160 mg (67%) of the title compound: $^1$H NMR (400 MHz, CD$_3$OD, mixture of rotamers) δ 7.47–7.25 (m, 12H), 7.06 (d, 1.2H, J=8 Hz), 6.95 (d, 0.8H, J=8 Hz), 6.80–6.75 (m, 1.6H), 6.52 (s, 0.4H), 5.12–4.90 (m, 5M), 4.06–4.00 (m, 0.6H), 3.85–3.78 (m, 0.4H), 3.30–3.20 (m, 1H), 3.00–2.92 (m, 2H), 2.78–2.49 (m, 2H), 0.41 (s, 3.6H), 0.23 (s, 5.4H).

Step C. 1-[[3'-Amino-(1,1'-biphenyl)-4-yl]methyl]-2-[(1,1-dimethylethoxy)-carbonyl]-6,7-bis(phenylmethoxy)-1,2,3, 4-tetrahYdroisoquinoline. To a solution of 30 mg (0.055 mmol) of the product from Example 6, Step B in 1 mL of toluene and 0.10 mL of ethanol, was added 0.40 mL of 2 M aqueous sodium carbonate solution, 15 mg (0.083 mmol) of 3-aminophenylboronic acid hemisulfate, and 6 mg (0.0055 mmol) of tetrakis(triphenylphosphine)palladium. The resultant mixture was stirred at 80° C. for 16 h, cooled, and diluted with ethyl acetate. The organic phase was washed sequentially with saturated aqueous sodium bicarbonate solution, water, and brine, dried over magnesium sulfate, and concentrated. The residue was purified by preparative TLC (silica gel, 25% ethyl acetate/hexane) to give 15 mg (49%) of the title compound: $^1$H NMR (400 MHz, CD$_3$OD, mixture of rotamers) δ 7.45–7.23 (m, 12H), 7.20–7.05 (m, 3H), 6.96 (s, 1H), 6.90 (d, 1H, J=8 Hz), 6.81–6.78 (m, 1H), 6.71–6.67 (m, 1.67H), 6.39 (s, 0.33H), 5.15–5.08 (m, 3H), 4.99 (s, 1.34H), 4.82 (s, 0.66H), 4.10–4.02 (m, 0.67H), 3.87–3.80 (m, 0.33H), 3.40 –3.25 (m, 1H), 3.05–2.95 (m, 2H), 2.80–2.53 (m, 2H), 0.41 (s, 31), 0.21 (s, 6H).

Step D. N-[4'-[(6,7-Dihydroxy-1,2,3,4-tetrahdro-1-isoquinolinyl)methyl]-[1,1'-biphenyl]-3-yl]-4-[[(hexylamino)carbonyl]amino]benzenesulfonamide, trifluoroacetate. In a manner analogous to that of Example 1, Step D, the title compound was prepared from the aniline in Example 6, Step C: $^1$H NMR (400 MHz, CD$_3$OD) δ 7.64 (d, 2H, J=8 Hz), 7.56 (d, 2H, J=8 Hz), 7.47–7.38 (m, 5H), 7.33–7.26 (m, 2H), 7.03–7.00 (m, 1H), 6.64 (s, 1H), 6.63 (s, 1H), 4.71–4.66 (m, 1H), 3.55–2.87 (m, 8H), 1.53–1.46 (m, 2H), 1.39–1.25 (m, 6H), 0.92–0.86 (m, 3H).

EXAMPLE 7

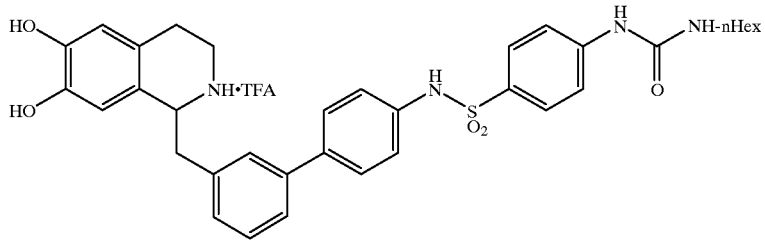

N-[3'-[(6,7-Dihydroxy-1,2,3,4-tetrahydro-1-isoquinolinyl) methyl][1,1'-biphenyl]-4-yl]-4-[[(hexylamino)carbonyl] amino]benzenesulfonamide, trifluoroacetate L-825,451

Step A. N-[2-[3,4-Bis(phenylmethoxy)phenyl]ethyl]-3-bromophenylacetamide. In a manner analogous to that of Example 6, Step A, the title compound was prepared from 3-bromophenylacetic acid in 61% yield: $^1$H NMR (400 MHz, CDCl$_3$) δ 7.45–7.03 (m, 14H), 6.80 (d, 1H, J=8 Hz), 6.68 (d, 1H, J=2 Hz), 6.49 (dd, 1H, J=2 and 8 Hz), 5.26–5.20 (m, 1H), 5.12 (s, 2H), 5.10 (s, 2H), 3.43–3.36 (m, 4H), 2.62 (t, 2H, J=8 Hz).

Step B. 1-[(3-Bromophenyl)methyl]-2-[(1,1-dimethylethoxy)carbony]-6,7-bis(phenylmethoxy)-1,2,3,4-tetrahydroisoquinoline. In a manner analogous to that of Example 6, Step B, the title compound was prepared from the amide in Example 7, Step A in 61% yield: $^1$H NMR (400 MHz, CD$_3$OD, mixture of rotamers) δ 7.48–7.02 (m, 14H), 6.82–6.79 (m, 1.67H), 6.58 (s, 0.33H), 5.13–4.80 (m, 5H), 4.10–4.03 (m, 0.67H), 3.88–3.80 (m, 0.33H), 3.30–3.23 (m, 1H), 3.01–2.90 (m, 2H), 2.78–2.49 (m, 2H), 0.40 (s, 3H), 0.22 (s, 6H).

Step C. 2-[(1,1-Dimethylethoxy)carbonyl]-1-[[4'-nitro-(1,1'-biphenyl)-3-yl]methyl]-6,7-bis(phenylmethoxy)-1,2,3,4-tetrahydroisoauinoline. To a solution of 50 mg (0.092 mmol) of the product from Example 7, Step B in 1 mL of toluene and 0.40 mL of ethanol was added 34.4 mg (0.138 mmol) of the pinacol ester of 4-nitrophenylboronic acid (J. Org. Chem. 1995, 60, 7508) and 3.8 mg (0.0046 mmol) of [1,1'-bis(diphenylphosphino)-ferrocene]dichloropalladium (II). The resultant mixture was purged with nitrogen, heated to 80° C. and 0.20 mL of 2 M aqueous cesium carbonate solution was added. The dark reaction mixture was then heated for a further 16 h, cooled, and diluted with ethyl acetate. The organic phase was washed sequentially with saturated aqueous sodium bicarbonate solution, water, and brine, dried over magnesium sulfate, and concentrated. The residue was purified by preparative TLC (silica gel, 25% ethyl acetatethexane) to give 48 mg (89%) of the title compound: 1H NMR (400 MHz, CD$_3$OD, mixture of rotamers) δ 8.30–8.24 (m, 2H), 7.81–7.73 (m, 2H), 7.62–7.53 (m, 1H), 7.48–7.15 (m, 1311), 6.83–6.79 (m, 1.67H), 6.48 (s, 0.33H), 5.21–5.13 (m, 1H), 5.10–4.90 (m, 4H), 4.10–4.02 (m, 0.67H), 3.85–3.78 (m, 0.33H), 3.38 –3.25 (m, 1H), 3.11–3.05 (m, 2H), 2.80–2.50 (m, 2H), 0.39 (s, 3H), 0.18 (s, 6H).

Step D. 1-[[4'-Amino-(1,1'-biphenyl)-3-yl]methyl]-2-(1,1-dimethylethoxy)-carbonyl]-6,7-bis(phenylmethoxy)-1,2,3,4-tetrahydroisoquinoline. In a manner analogous to that of Example 1, Step C, the title compound was prepared from the nitro compound in Example 7, Step C in 59% yield: $^1$H NMR (400 MHz, CD$_3$OD, mixture of rotamers) δ 7.45–7.20 (m, 14.67H), 7.11 (2, 0.33H), 7.02 (d, 0.67H, J=8 Hz), 6.93 (d, 0.33H, J=8 Hz), 6.81–6.74 (m, 3H), 6.70 (s, 0.67H), 6.46 (s, 0.33H), 5.15–5.06 (m, 3H), 4.99 (s, 1.34H), 4.85 (s, 0.66H), 4.08–4.00 (m, 0.67H), 3.83–3.74 (m, 0.33H), 3.38 –3.26 (m, 1H), 3.06–2.99 (m, 2H), 2.80–2.48 (m, 2H), 0.41 (s, 3H), 0.21 (s, 6H).

Step E. N-[3'-[(6,7-Dihydroxy-1,2,3,4-tetrahydro-1-isoquinolinyl)methyl][1,1'-biphenyl]-4-yl]-4-[[(hexylamino)carbonyl]amino]benzene-sulfonamide, tifluoroacetate. In a manner analogous to that of Example 1, Step D, the title compound was prepared from the aniline in Example 7, Step D: $^1$H NMR (400 MHz, CD$_3$OD) δ 7.64 (d, 2H, J=8 Hz), 7.53–7.41 (m, 7H),7.28 (d, 1H, J=9 Hz), 7.18 (d, 2H, J=8 Hz), 6.63(s, 2H), 4.73–4.69 (m, 1H), 3.55–2.85 (m, 8H), 1.53–1.46 (m, 2H), 1.39–1.25 (m, 6H), 0.92–0.86 (m, 3H).

EXAMPLE 8

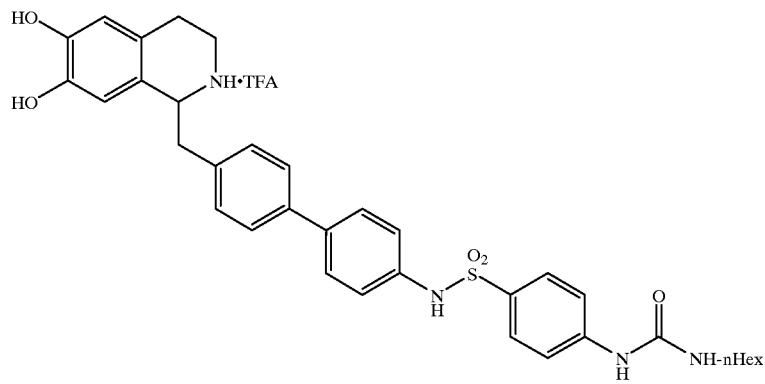

N-[4'-[(6,7-Dihydroxy-1,2,3,4-tetrahydro-1-isoquinolinyl)methyl][1,1'-biprhenyl]-4-yl]-4-[[(hexylamino)arbonyl]amino]benzenesulfonamide. trifluoroacetate L-825,452

In a manner analogous to that of Example 7, Steps C, D, and E, the title compound was prepared from the bromide in Example 6, Step B: $^1$H NMR (400 MHz, CD$_3$OD) δ 7.66 (d, 2H, J=8.6 Hz), 7.60 (d, 2H, J=8 Hz), 7.51 (d, 2H, J=9 Hz), 7.46 (d, 2H, J=8.6 Hz), 7.36 (d, 2H, J=9 Hz), 7.18 (d, 2H, J=8 Hz), 6.63 (s, 1H), 6.61 (s, 1H), 4.70–4.66 (m, 1H), 3.51–3.45 (m, 2H), 3.30–3.22 (m, 1H), 3.17 (t, 2H, J=7.2 Hz), 3.13–2.87 (m, 3H), 1.53–1.46 (m, 2H), 1.38–1.27 (m, 6H), 0.92–0.87 (m, 3H).

Following the procedures outlined for Example 8, the compounds listed in Table 2 were prepared.

TABLE 2

| Ex. | R | Selected $^1$H NMR (CD$_3$OD) Data |
|---|---|---|
| 9 | 4-iodophenyl L-825,831 | 7.87(d, 2H, J=10 Hz), 7.54-7.48(m, 4H). |
| 10 | 4-[4-[4-(trifluoromethyl)phenyl]thiazol-2-yl]phenyl L-825,832 | 8.21–8.10(m, 5H), 7.90(d, 2H, J=9 Hz), 7.72(d, 2H, J=9 Hz). |
| 11 | 3-quinolinyl L-825,980 | 9.07(d, 1H, J=2 Hz), 8.79(d, 1H, J=2 Hz), 8.10–8.03(m, 2H), 7.92(d, 1H, J=8Hz), 7.72 (d, 1H, J=8 Hz). |
| 12 | 4-(trifluoromethoxy)phenyl L-825,981 | 7.89(d, 2H, J=9 Hz), 7.41–7.35(m, 4H). |
| 13 | methyl L-828,283 | 2.99(s, 3H). |

EXAMPLE 14

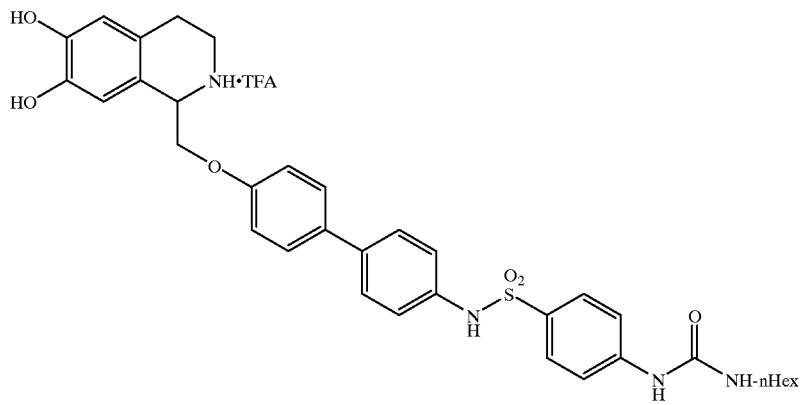

N-[4'-[(6,7-Dihydroxy-1,2,3,4-tetrahydro-1-isoquinolinyl)methoxy][1,1-biphenyl]-4-yl]-4-[[(hexlamino)carbonyl]amino]benzenesulfonamide. trifluoroacetate L-828,710

Step A. Methyl 2-Bromophenoxyacetate. To a stirred solution of 1.0 g (5.8 mmol) of 4-bromophenol in 20 mL of dimethylformamide was added 1.89 g (5.8 mmol) of cesium carbonate. The resultant mixture was stirred at ambient temperature for 45 minutes, then a solution of 887 mg (5.8 mmol) of methyl bromoacetate in 4 mL of dimethylformamide was added. After stirring at ambient temperature for 3 h the mixture was poured into a separatory funnel containing ice and water. It was then extracted with 3 portions of ethyl acetate and the combined organic phases were washed with one portion each of water and brine, dried over magnesium sulfate, and concentrated to give 1.42 g (100%) of the title compound which was used without further purification: $^1$H NMR (400 MHz, CDCl$_3$) δ 7.37 (d, 2H, J=9.13 Hz), 6.77 (d, 2H, J=9.13 Hz), 4.59 (s, 2H), 3.78 (s, 3H).

Step B. 4-Bromophenoxyacetic acid. To a solution of 1.42 g (5.8 mmol) of the product from Example 14, Step A in 40 mL of methanol was added 15 mL of 5 N aqueous sodium hydroxide. After stirring for 4 h at ambient temperature the solvent was removed in vacuo, then the residue was suspended in water and acidified to pH 2 with concentrated hydrochloric acid. The resultant solid was collected by filtration and dried under vacuum to give 1.15 g (86%) of the title compound as a white solid: $^1$H NMR (400 MHz, CD$_3$OD) δ 7.39 (d, 2H, J=9.1 Hz), 6.86 (d, 2H, J=9.1 Hz), 4.63 (s, 2H).

Step C. N-[2-[3,4-Bis(phenylmethozy)phenyl]ethyl]-4-bromophenoxyacetamide. To a solution of 350 mg of the product from Example 14, Step B in 15 mL of dichloromethane at 0° C. was added 0.90 mL (1.8 mmol) of oxalyl chloride (2.0 M in dichloromethane) and 0.10 mL of dimethylformamide. The mixture was stirred at ambient temperature for 4 h and the solvent was removed in vacuo. The residue was suspended in 5 mL of dichloromethane and added to a mixture of 610 mg (1.65 mmol) of 3,4-bis(benzyloxy)phenethylamine hydrochloride and 1.05 mL (7.53 mmol) of triethylamine at 0° C. The resulting mixture was stirred at ambient temperature for 16 h, then diluted with dichloromethane and washed sequentially with one portion each of water and brine. The organic layer was dried over magnesium sulfate, concentrated in vacuo and the residue purified by radial chromatography (silica gel, 30% ethyl acetate/hexane) to give 730 mg (81%) of the title compound: $^1$H NMR, (300 MHz, CDCl$_3$) δ 7.46–7.26 (m, 12H), 6.85–6.5 (m, 6H), 5.14 (s, 2H), 5.12 (s, 2H), 4.42 (s, 2H), 3.57–3.50 (m, 2H), 2.75 (t, 2H, J=6.87 Hz).

Step D. 1-[(4-Bromophenyl)methoxy]-2-[(1,1-dimethylethoxy)carbonyl]-6,7-bis(phenylmethoxy)-1,2,3,4-tetrahydroisoquinoline. To a solution of 730 mg (1.34 mmol) of the product from Example 14 Step C in 4 mL of acetonitrile was added 1 mL of phosphorous oxychloride.

The resultant mixture was stirred at 80° C. for 2 hours then was concentrated in vacuo, dissolved in ethyl acetate, and added to a separatory funnel containing ice and water. The organic layer was washed with 2 N sodium hydroxide and brine then was dried over magnesium sulfate and concentrated in vacuo. The residue was suspended in 2 mL of ethanol, cooled to 0° C. and 126 mg (3.35 mmol) of sodium borohydride added in several portions. The resultant mixture was stirred at ambient temperature for 1 h, concentrated, and partitioned between ethyl acetate and water. The layers were separated and the organic layer washed with brine, dried over magnesium sulfate, and concentrated in vacuo to give 391 mg of product. The residue was immediately dissolved in 10 mL of tetrahydrofuran and 194 mg (0.89 mmol) of di-t-butyldicarbonate was added. The resultant mixture was stirred at ambient temperature for 3 h, diluted with ethyl acetate, washed sequentially with saturated aqueous sodium bicarbonate solution and brine, dried over magnesium sulfate and concentrated. The residue was purified by radial chromatography (silica gel, 20% ethyl acetate/hexane) to give 274 mg (32%) of the title compound as a white solid. $^1$H NMR (400 MHz, CD$_3$OD, mixture of rotamers) δ 7.44–7.26 (m, 12H), 6.9–6.75 (m, 4H), 5.3 (m, 1H), 5.08 (s, 4H), 4.2–3.9 (m, 3H), 3.45–3.2 (m, 1H), 2.8–2.6 (m, 2H), 1.47 (s, 3.6H), 1.41 (s, 5.4H).

Step E. 2-[(1,1-Dimethylethoxy)carbonyl]-1-[[4'-nitro-(1,1'-biphenyl)-4-yloxy]methyl]-6,7-bis(phenylmethoxy)-1,2,3,4-tetrahydroisoquinoline. To a solution of 100 mg (0.16 mmol) of the product from Example 14 Step D in 2 mL of toluene and 800 mL of ethanol, was added 70 mg (0.28 mmol) of the pinacol ester of 4-nitrophenylboronic acid and 6.5 mg (0.008 mmol) of [1,1'-bis(diphenylphosphino)-ferroceneldichloropalladium(II). The resultant mixture was purged with nitrogen, heated to 80° C. and 0.400 mL of 2 M aqueous cesium carbonate solution was added. The dark reaction mixture was then heated at 80° C. for an additional 16 h, cooled, and diluted with ethyl acetate. The organic phase was washed with one portion each of water and brine, then dried over magnesium sulfate and concentrated. The residue was purified by radial chromatography (silica gel, 20% ethyl acetate/hexane) to give 66 mg (61%) of the title compound: $^1$H NMR (400 MHz, CD$_3$OD), mixture of rotamers) δ 8.28 (d, 2H, J=8 Hz), 7.82 (d, 2H, J=8 Hz), 7.7–7.6 (m, 2H), 7.45–7.25 (m, 10H), 7.05–6.98 (m, 2H), 6.95 (s, 1H), 6.85 (s, 1H), 5.4–5.3 (m, 1H), 5.1 (s, 4H), 4.3–3.9 (m, 3H), 3.5–3.25 (m, 1H), 2.8–2.65 (m, 2H), 1.5 (s, 4.3H), 1.4 (s, 4.7H).

Step F. N-[4'-[(6,7-Dihydroxy-1,2,3,4-tetrahydro-1-isoquinolinyl)methoxy]-[1,1'-biphenyl]-4-yl]-4-[[(hexylamino)carbonyl]amino]benzenesulfonamide, trifluoroacetate. To a solution of 66 mg (0.098 mmol) of the product from Example 14 Step E in 10 mL of methanol and 5 mL of ethyl acetate was added palladium hydroxide on activated carbon and the mixture stirred under 1 atmosphere of hydrogen at ambient temperature for 15 minutes. The solution was filtered through celite, the filtrate concentrated, and one-half of the residue (20 mg, 0.043 mmol) suspended in 2 mL of dichloromethane. The solution was cooled to 0° C. and 0.5 mL of pyridine and 22 mg (0.069 mmol) of 4-[[(hexylamino)carbonyl]amino]benzenesulfonyl chloride were added. The resultant mixture was stirred at ambient temperature for 16 h, concentrated, and the residue purified by preparative TLC (silica gel, 2% methanol/dichloromethane) to give 22 mg (69%) of the N-BOC protected title compound: $^1$H NMR (400 MHz, CD3OD) δ 7.62 (d, 2H, J=8.85 Hz), 7.5–7.38 (m, 6H), 7.1 (d, 2H, J=8.2 Hz), 7.0–6.9 (m, 2H), 6.68 (s, 1H), 6.56 (s, 1H), 5.32–5.25 (m, 1H), 4.25–3.9 (m, 3H), 3.5–3.2 (m, 1H), 3.15 (t, 2H, J=7 Hz), 2.8–2.6 (m, 2H), 1.55–1.25 (m, 17H), 0.9 (m, 3H). To a solution of 22 mg (0.029 mmol) of the N-Boc protected title compound in 2 mL of dichloromethane at 0° C. was added 2 mL of trifluoroacetic acid. The resultant mixture was stirred at ambient temperature for 1.5 h, concentrated in vacuo, and the excess trifluoroacetic acid removed by azeotropic distillation with dichloromethane and methanol to provide 19 mg (86%) of the title compound: $^1$H NMR (400 MHz, CD$_3$OD) δ 7.63 (d, 2H, J=8.81 Hz), 7.51, (d, 2H, J=8.81 Hz), 7.47–7.41 (m, 4H), 7.13 (d, 2H, J=8.62 Hz), 7.08 (d, 2H, J=11.8 Hz), 6.76 (s, 1H), 6.66 (s, 1H), 4.85–4.82 (m, 1H), 4.55 (dd, 1H, J=10.7, 3.87 Hz), 4.30 (m, 1H), 3.62–3.34 (m, 2H), 3.15 (t, 2H, J=7.05 Hz), 3.05–2.95 (m, 2H), 1.51–1.47 (m, 2H),1.38–1.28 (m, 6H), 0.91–0.87 (m, 3H).

EXAMPLE 15

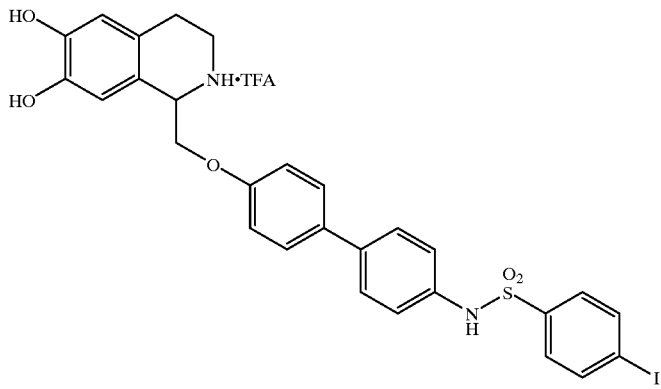

N-[4'-[(6,7-Dihydroxy-1,2,3,4-tetrahydro-1-isoquinolinyl)methoxyl][1,1'-biphenl]-4-yl]-4-iodobenzenesulfonamide, trifluoroacetate L-828,711

Following the procedure outlined in Example 14, the title compound was prepared using 4-iodobenzenesulfonyl chloride: $^1$H NMR (400 MHz, CD$_3$OD) δ 7.86 (d, 2H, J=8.62 Hz), 7.53–7.44 (m, 6H), 7.15–7.08 (m, 4H), 6.76 (s, 1H), 6.67 (s, 1H), 4.85–4.80 (m, 1H), 4.56 (dd, 1H, J=10.76, 3.81 Hz), 4.33–4.28 (m, 1H), 3.61–3.31 (m, 2H), 3.01–2.98 (m, 2H).

EXAMPLE 16

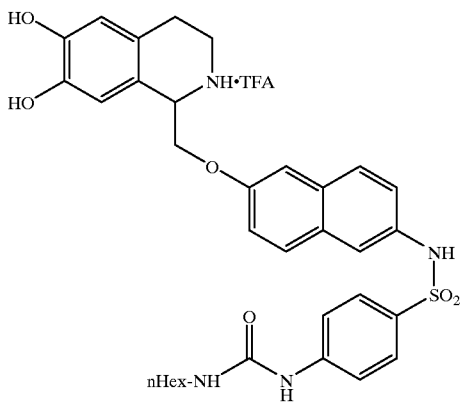

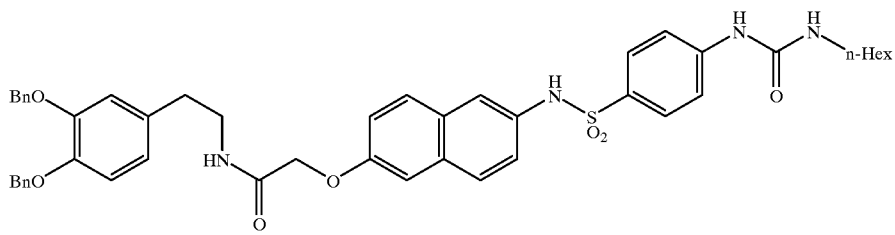

N-[6-[(6,7-Dihydroxy-1,2,3,4-tetrahydro-1-isoquinolinyl)
methoxy]naphth-2-yl]-4-[[(hexylamino)carbonyl]amino]
benzenesulfonamide, trifluoroacetate L-825,695

Step A. 6-Amino-2-naphthol. A mixture of 10.0 g (45 mmol) of 6-bromo-2-naphthol, 495 mg (5 mmol) of copper(I) chloride, 572 mg (9 mmol) of copper powder, and 26 mL of 28% ammonium hydroxide were heated at 150° C. in a stainless steel bomb for 14 h. The crude reaction mixture was suspended in dichloromethane and the copper solids removed by filtration. The filtrate was concentrated and purified by flash column chromatography (silica gel, 5% methanol/0.5% ammonium hydroxide/dichloromethane) to give 2.8 g (39%) of the title compound: $^1$H NMR (400 MHz, CDCl$_3$) δ 7.90 (s, 1H), 7.64 (d, 1H, J=9.6 Hz), 7.54–7.45 (m, 2H), 7.1–7.08 (m, 2H), 4.95 (br s, 1H), 1.6 (br s, 2H).

Step B. 6-Hydroxynaphth-2-ylcarbamic acid, 1,1-dimethylethyl ester. To a solution of 740 mg (4.65 mmol) of the product from Example 16, Step A in 15 mL of 1,4-dioxane was added 1.01 g (4.65 mmol) of di-tert-butyldicarbonate. The resultant mixture was heated at 80° C. for 4 h then was diluted with ethyl acetate and washed with one portion each of water and brine. The organic layer was dried over magnesium sulfate, concentrated, and the residue purified by flash column chromatography (silica gel, 15% ethyl acetate/hexane) to give 1.0 g (83%) of the title compound: $^1$H NMR (400 MHz, CDCl$_3$) δ 7.89 (br s, 1H), 7.63 (d, 1H, J=8.75), 7.56 (d, 1H, J=8.91), 7.25 (m, 2H), 7.05–7.02 (m, 2H), 6.53 (br s, 1H), 5.0 (br s, 1H), 1.38 (s, 9H).

Step C. N-[2-[3,4-Bis(phenylmethoxy)phenyl]ethyl]-6-[[(1,1-dimethylethoxy)carbonyl]amino]-2-naphthyloxyacetamide. The product from Example 16, Step B was converted to the title compound in a manner analogous to that of Example 14, Steps A, B, and C: $^1$H NMR (400 MHz, CDCl$_3$) δ 7.95 (br s, 1H), 7.65–7.60 (m, 2H), 7.45–7.24 (m, 10H), 7.0 (m, 2H), 6.78–6.72 (m, 2H), 6.60–6.52 (m, 3H), 5.10 (s, 2H), 5.05 (s, 2H), 4.54 (s, 2H), 3.55–3.5 (m, 2H), 2.70 (t, 2H, J=6 Hz), 1.57 (s, 3.4H), 1.52 (s, 5.6H).

Step D. N-[2-[3,4-Bis(phenylmetho)phenyl]ethyl]-6-amino-2-naphthyloxyacetamide. The product from Example 16, Step C was treated in a manner analogous to that of Example 14, Step F to give the title compound in 64% yield following purification by radial chromatography (silica gel, 5% methanol/0.5% ammonium hydroxide/dichloromethane): $^1$H NMR (400 MHz, CDCl$_3$) δ 8.0–7.0 (m, 13H), 6.8–6.5 (m, 6H), 5.1 (s, 2H), 5.09 (s, 2H), 4.55 (s, 2H), 3.57–3.5 (m, 2H), 2.75–2.70 (m, 2H).

Step E. N-[6-[[[[2-[3,4-Bis(phenylmethoxy)phenl]ethyl]amino]carbonyl]methoxy]naphth-2-yl]-4-[[(hexylamino) carbonyl]amino] benzenesulfonamide. To a solution of 45 mg (0.084 mmol) of the product from Example 16, Step D in 2 mL of dichloromethane at 0° C. was added 0.20 mL of pyridine and 49 mg (0.15 mmol) of 4-[[(hexylamino) carbonyl]amino]benzenesulfonyl chloride. The resultant mixture was stirred at ambient temperature for 16 h, concentrated, and the residue purified by preparative TLC (silica gel, 2% methanol/dichloromethane) to give 61 mg (95%) of the title compound: $^1$H NMR (400 MHz, CD$_3$OD) δ 7.85 (s, 1H), 7.62–7.58 (m, 4H), 7.46–7.08 (m, 13H), 6.88 (m, 1H), 6.75 (m, 1H), 6.60 (m, 1H), 5.01 (s, 4H), 4.53 (s, 2H), 3.52–3.10 (m, 6H), 2.72 (m, 2H), 1.50–1.25 (m, 8H), 0.91–0.87 (m, 3H).

Step F. N-[6-[(6,7-Dihydroxy-1,2,3,4-tetrahydro-1-isoquinolinyl)methoxy]naphth-2-yl]-4-[[(hexylamino) carbonyl]amino]benzenesulfonamide, trifluoroacetate. To a solution of 61 mg (0.08 mmol) of the product from Example 16, Step E in 1 mL of acetonitrile was added 0.25 mL of phosphorous oxychloride. The resultant mixture was stirred at 80° C. for 4 h, concentrated, and suspended in chloroform. The organic layer was washed with 2 N aqueous sodium hydroxide solution and brine then was dried over magnesium sulfate and concentrated in vacuo. The residue was suspended in 1 mL of ethanol, cooled to 0° C. and 8 mg (0.21 mmol) of sodium borohydride was added. The mixture was stirred at ambient temperature for 16 h, concentrated, and partitioned between ethyl acetate and water. The layers were separated and the organic layer was washed with brine, dried over magnesium sulfate and concentrated in vacuo. The residue was purified by preparative TLC (silica gel,5% methanol. methylene chloride) to give 10 mg of product.

This was suspended in 3 mL of methanol and 3 mL of 12 N hydrochloric acid was added. The resultant mixture was heated at 60° C. for 16 h, then at 80° C. for 24 h, then was concentrated and the residue purified by preparative TLC (silica gel, 10% methanol/1% ammonium hydroxide/ dichloromethane). The product was dissolved in dichloromethane and methanol and trifluoroacetic acid was added. After standing for several hours at ambient temperature the solvent was removed in vacuo and the excess trifluoroacetic acid removed by azeotropic distillation with dichloromethane to provide 1.7 mg (3%) of the title compound: $^1$H NMR (400 MHz, CD$_3$OD) δ 7.67–7.64 (m, 2H), 7.6 (d, 2H, J=8.9 Hz), 7.47 (m, 1H), 7.4 (d, 2H, J=8.9 Hz), 7.30–7.20 (m, 3H), 6.78 (s, 1H), 6.67 (s, 1H), 5.0–4.8 (m, 1H), 4.65 (dd, 1H, J=10,4 Hz), 4.40–4.34 (m, 1H), 3.65–3.35 (m, 2H), 3.14 (t, 2H, J=7.1 Hz), 3.04–2.95 (m, 2H), 1.53–1.45 (m, 2H), 1.40–1.25 (m, 6H), 0.94–0.85 (m, 3H).

EXAMPLE 17

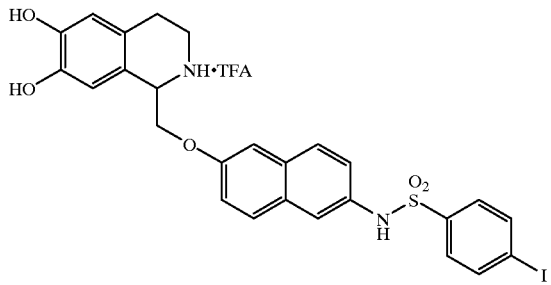

N-[6-[(6,7-dihydroxy-1,2,3,4-tetrahydro-1-isoquinolinyl) methoxy]naphth-2-yl]-4-iodobenzenesulfonamide, trifluoroacetate L-825,694 Following the procedure outlined in Example 16, Steps E and F, the title compound was prepared using 4-iodobenzenesulfonyl chloride: $^1$H NMR (400 MHz, CD$_3$OD) δ 7.8 (d, 2H, J=8.67 Hz), 7.67 (d, 2H, J=8.76 Hz), 7.48 (m, 1H), 7.45 (d, 2H, J=8.67 Hz), 7.31–7.18 (m, 3H), 6.78 (s, 1H), 6.67 (s, 1H), 4.9–4.8 (m, 1H), 4.62 (dd, 1H, J=10.75, 3.92 Hz), 4.40–4.35 (m, 1H), 3.62–3.39 (m, 2H), 3.02–2.98 (m, 2H).

EXAMPLE 18

N-[4'-[(7-Hydroxy-1,2,3,4-tetrahydro-1-isoquinolinyl) methyl][1,1'-biphenyl]-4-yl]-4-[[(hexylamino)carbonyl] amino]benzenesulfonamide, trifluoroacetate. L-829,391

Step A. N-[2-(4-Methoxyphenyl)ethyl]-4-bromophenylacetamide. In a manner analogous to that of Example 6, Step A, the title compound was prepared from 4-methoxyphenethylamine in 80% yield: $^1$H NMR (400 MHz, CDCl$_3$) δ 7.42 (d, 2H, J=8 Hz), 7.03 (d, 2H, J=8 Hz), 6.90 (d, 2H, J=8 Hz), 6.77 (d, 2H, J=8 Hz), 5.28–5.20 (m, 1H), 3.78 (s, 3H), 3.45–3.38 (m, 4H), 2.64 (t, 2H, J=8 Hz).

Step B. 1-[(4-Bromophenyl)methyl]-2-[(1,1-dimethylethoxy)carbonyl]-7-methoxy-1,2,3,4-tetrahydroisoquinoline. To 450 mg (1.29 mmol) of the product from Example 18, Step A was added 5 g of polyphosphate ester. The resultant mixture was stirred at 80° C. for 20 h, cooled, and added to ice/water. Saturated aqueous potassium carbonate solution was added until the aqueous phase was basic. The resultant mixture was extracted with chloroform, washed with brine, dried over magnesium sulfate, and concentrated in vacuo to give a yellow oil. This residue was immediately suspended in 6 mL of ethanol and 122.5 mg (3.22 mmol) of sodium borohydride was added portionwise. The resultant mixture was stirred at ambient temperature for 2 h, concentrated, and partioned between ethyl acetate and water. The layers were separated, the aqueous phase back extracted with ethyl acetate, and the combined organic phases were washed with brine, dried over magnesium sulfate, and concentrated in vacuo. The residue was purified by radial chromatography (silica gel, 50% ethyl acetate/20% hexane/30% methylene chloride) to give 163 mg (38%) of product. This was immediately dissolved in 8 mL of THF and 129 mg (0.588 mmol) of di-t-butyldicarbonate was added. The resultant mixture was stirred at ambient temperature for 16 h, and concentrated. The residue was purified by preparative TLC (silica gel, 20% ethyl acetate/hexane) to give 189 mg (89%) of the title compound: $^1$H NMR (400 MHz, CD$_3$OD, mixture of rotamers) δ 7.43 (d, 1.24H, J=7.2 Hz), 7.37 (d, 0.76H, J=9 Hz), 7.12 (d, 1.24H, J=7.2 Hz), 7.17–7.00 (m, 1.76H), 6.78–6.69 (m, 1.62H), 6.52 (s, 0.38H), 5.23–5.12 (m, 1H), 4.09–4.02 (m, 0.62H), 3.87–3.70 (m, 0.38H), 3.75 (s, 1.87H), 3.68 (s, 1.13H), 3.41 –3.30 (m, 1H), 3.09–2.96 (m, 2H), 2.81–2.48 (m, 2H), 0.38 (s, 3.4H), 0.21 (s, 5.6H).

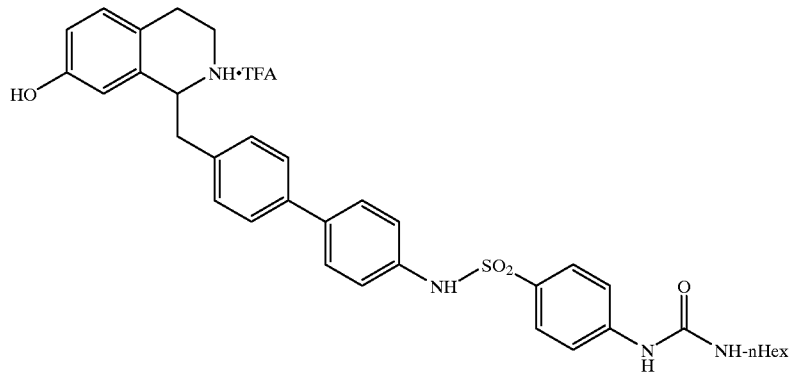

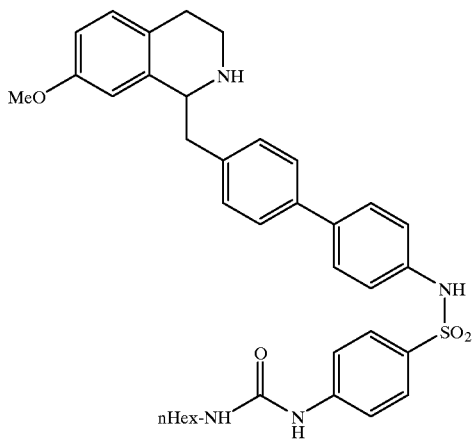

Step C. N-[4'-[(7-Methoxy-1,2,3,4-tetrahydro-1-isoquinolinyl)methyl][1,1'-biphenyl]-4-yl]-4-[[(hexylamino)carbonyl]amino]benzenesulfonamide. In a manner analogous to that of Example 14, Steps E, F, and G, the title compound was prepared from the bromide in Example 18, Step B: $^1$H NMR (400 MHz, CD$_3$OD) δ 7.66 (d, 2H, J=9.6 Hz), 7.60 (d, 2H, J=8 Hz), 7.49 (d, 2H, J=9 Hz), 7.46 (d, 2H, J=9.6 Hz), 7.37 (d, 2H, J=9 Hz), 7.20–7.15 (m, 3H), 6.88 (dd, 1H, J=9 and 2 Hz), 6.62 (d, 1H, J=2 Hz), 4.83–4.78 (m, 1H), 3.64 (s, 3H), 3.60–3.48 (m, 2H), 3.37–3.30 (m, 1H), 3.22–2.97 (m, 5H), 1.53–1.47 (m, 2H), 1.38–1.27 (m, 6H), 0.92–0.87 (m, 3H).

Step D. N-[4'-[(7-Hydroxy-1,2,3,4-tetrahydro-1-isoquinolinyl)methyl][1,1'-biphenyl]-4-yl]-4-[[(hexylamino)carbonyl]amino]benzenesulfonamide, trifluoroacetate. To a suspension of 42 mg (0.067 mmol) of the product from Example 18, Step C in 4 mL of dichloromethane at −78° C. was added 0.335 mL of a 1 M solution of boron tribromide in dichloromethane. The resultant mixture was stirred at −78° C. for 5 min, warmed to ambient temperature and stirred for a further 2.5 h. The reaction was quenched with methanol, concentrated in vacuo, and the trimethylborate removed by azeotropic distillation with methanol. The residue was purified by preparative TLC (silica gel, 10% methanol/1% ammonium hydroxide/dichloromethane) to give 19 mg (46%) of product which was dissolved in dichloromethane and trifluoroacetic acid was added. After standing at ambient temperature, the solvent was removed in vacuo and the excess trifluoroacetic acid removed by azeotropic distillation with dichloromethane to provide the title compound: $^1$H NMR (400 MHz, CD$_3$OD) δ 5 7.66 (d, 2H, J=9 Hz), 7.60 (d, 2H, J=8 Hz), 7.50 (d, 2H, J=9 Hz), 7.46 (d, 2H, J=8 Hz), 7.38 (d, 2H, J=9 Hz), 7.19 (d, 2H, J=9 Hz), 7.09 (d, 1H), J=9 Hz), 6.78 (dd, 1H, J=9 and 2 Hz), 6.65 (d, 1H, J=2 Hz), 4.80–4.74 (m, 1H), 3.56–3.48 (m, 2H), 3.33–3.27 (m, 1H), 3.19–2.92 (m, 5H), 1.54–1.46 (m, 2H), 1.39–1.25 (m, 6H), 0.92–0.87 (m, 3H).

EXAMPLE 19

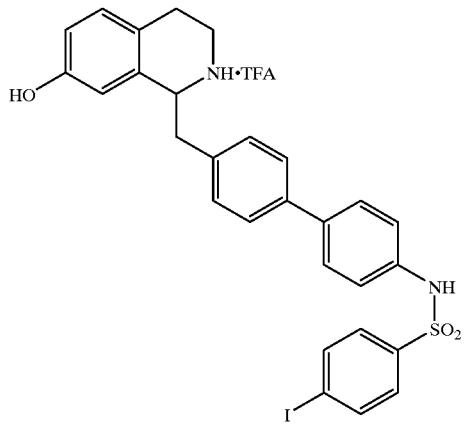

N-[4'-[(7-Hydroxy-1,2,3,4-tetrahydro-1-isoquinolinyl)methyl][1,1'-biphenyl]-4-yl]-4-iodobenzenesulfonamide, trifluoroacetate. L-829,392 Following the procedure outlined in Example 18, the title compound was prepared: $^1$H NMR (400 MHz, CD$_3$OD) δ 7.88 (d, 2H, J=9.6 Hz), 7.61 (d, 2H, J=8 Hz), 7.57–7.49 (m, 4H), 7.39 (d, 2H, J=8 Hz), 7.19 (d, 2H, J=9 Hz), 7.09 (d, 1H, J=9 Hz), 6.78 (dd, 1H, J=9 and 2 Hz), 6.65 (d, 1H, J=2 Hz), 4.80–4.74 (m, 1H), 3.58–3.49 (m, 2H), 3.33–3.27 (m, 1H), 3.19–2.95 (m, 3H).

What is claimed is:

1. A compound having the formula I:

$$\text{(R}^1\text{)}_m \text{—[isoquinoline-NH]—W—(B)—(C)—NHSO}_2\text{—(Z)—(R}^{1a}\text{)}_p \quad \text{I}$$

wherein m and p are independently 0 to 5;

W is
 (1) a bond,
 (2) $C_1$–$C_5$ alkylene,
 (3) $C_1$–$C_5$ alkylene wherein said alkylene contains an oxygen, with the proviso that the oxygen is not directly attached to the piperidine ring;

B is
 (1) phenyl,
 (2) naphthyl,
 (3) a 5 or 6-membered heterocyclic ring with from 1 to 4 heteroatoms selected from oxygen, sulfur and nitrogen,
 (4) a benzene ring fused to a $C_5$–$C_{10}$ carbocyclic ring,
 (5) a benzene ring fused to a 5 or 6-membered heterocyclic ring with from 1 to 4 heteroatoms selected from oxygen, sulfur and nitrogen,
 (6) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or (7) a 5 or 6-membered heterocyclic ring with from 1 to 4 heteroatoms selected from oxygen, sulfur and nitrogen fused to a $C_5$–$C_{10}$ carbocyclic ring;

C is
 (1) B, or
 (2) a bond;

Z is
 (1) B,
 (2) $C_1$–$C_{10}$ alkyl optionally substituted with B-$(R^{1a})_p$, with the proviso that when B and C are both phenyl, Z is B or $C_1$–$C_{10}$ alkyl substituted with B-$(R^{1a})_p$;

$R^1$ and $R^{1a}$ are independently
 (1) $C_1$–$C_{10}$ alkyl optionally substituted with up to 5 groups selected from
  (a) Q'$CO_2R^2$,
  (b) halogen,
  (c) cyano,
  (d) $QR^2$,
  (e) $C_3$–$C_8$ cycloalkyl,
  (f) B optionally substituted with up to 5 groups selected from halogen, $R^2$, $QR^2$, oxo, and $CO_2R^2$;
  (g) Q'$COR^3$,
  (h) $S(O)_nNR^2R^2$, where n is 0 to 2, and
  (i) $NR^2SO_2R^3$;
 (2) $C_3$–$C_8$ cycloalkyl,
 (3) oxo,
 (4) halogen,
 (5) cyano,
 (6) $QR^2$,
 (7) $S(O)_nNR^2R^2$, where n is 0 to 2,
 (8) Q'$COR^3$,
 (9) $NR^2SO_2R^3$,
 (10) Q'$CO_2R^2$, or
 (11) B optionally substituted with up to 5 groups independently selected from
  (a) $R^2$,
  (b) $QR^2$,
  (c) halogen, and
  (d) oxo;

$R^2$ is
 (1) hydrogen,
 (2) $C_1$–$C_{10}$ alkyl optionally substituted with up to 5 groups selected from
  (a) hydroxy,
  (b) halogen,
  (c) $CO_2R^4$,
  (d) $S(O)_n$—$C_1$–$C_{10}$ alkyl, where n is 0 to 2,
  (e) $C_3$–$C_8$ cycloalkyl,
  (f) $C_1$–$C_{10}$ alkoxy, and
  (g) B optionally substituted with up to 5 groups selected from halogen, trifluoromethyl, trifluoromethoxy, cyano, $C_1$–$C_{10}$ alkyl and $C_1$–$C_{10}$ alkoxy,
 (3) $C_3$–$C_8$ cycloalkyl, or
 (4) B optionally substituted with up to 5 groups selected from
  (a) halogen,
  (b) nitro,
  (c) oxo,
  (d) $NR^4R^4$,
  (e) $C_1$–$C_{10}$ alkoxy, optionally substituted with up to 5 halogens,
  (f) $S(O)_n$—$C_1$–$C_{10}$ alkyl where n is 0 to 2,
  (g) $C_1$–$C_{10}$ alkyl optionally substituted with up to 5 groups selected from hydroxy, halogen, trifluoromethyl, cyano, $CO_2R^4$, $C_3$–$C_8$ cycloalkyl, $S(O)_n$—$R^5$ where n is 0 to 2, $OR^5$, and $NR^4R^4$,
  (h) hydroxy, and
  (i) cyano;

$R^3$ is
 (1) $R^2$ or
 (2) $NR^2R^2$;

$R^4$ is
 (1) H, or
 (2) $C_1$–$C_{10}$ alkyl;

$R^5$ is
 (1) B optionally substituted with up to 5 groups selected from halogen, trifluoromethyl, trifluoromethoxy, cyano, $C_1$–$C_{10}$ alkyl and $C_1$–$C_{10}$ alkoxy, or
 (2) $C_1$–$C_{10}$ alkyl;

Q is
 (1) $N(R^2)$,
 (2) O or
 (3) $S(O)_n$, and n is 0 to 2;

Q' is
 (1) $N(R^2)$,
 (2) O or
 (3) a bond; or a pharmaceutically acceptable salt thereof.

2. A compound of claim 1 wherein B is phenyl or naphthyl.

3. A compound of claim 1 wherein C is a bond or phenyl.

4. A compound of claim 1 wherein Z is phenyl or a benzene ring fused to a 5- or 6-membered heterocyclic ring with from 1 to 4 heteroatoms selected from oxygen, sulfur and nitrogen.

5. A compound of claim 1
wherein

W is (1) $C_1$–$C_5$ alkylene or
 (2) $C_1$–$C_5$ alkyleneoxy wherein the oxygen is attached to B;

B is (1) phenyl or
 (2) naphthyl;

C is (1) a bond or
 (2) phenyl;

Z is (1) phenyl or
 (2) a benzene ring fused to a 5- or 6-membered heterocyclic ring with from 1 to 4 heteroatoms selected from oxygen, sulfur and nitrogen;

$R^1$ is (1) $C_1$–$C_{10}$ alkyl optionally substituted with up to 5 groups selected from
  (a) Q'$CO_2R^2$,
  (b) halogen,
  (c) cyano,
  (d) $QR^2$,
  (e) Q'$COR^3$,
  (f) $S(O)_nNR^2R^2$, where n is 0 to 2, and
  (g) $NR^2SO_2R^3$;
 (2) halogen,
 (3) cyano,
 (4) $QR^2$,
 (5) $S(O)_nNR^2R^2$, where n is 0 to 2,
 (6) Q'$COR^3$,
 (7) $NR^2SO_2R^3$, or
 (8) Q'$CO_2R^2$.

6. A compound of claim 1 having the formula Ia:

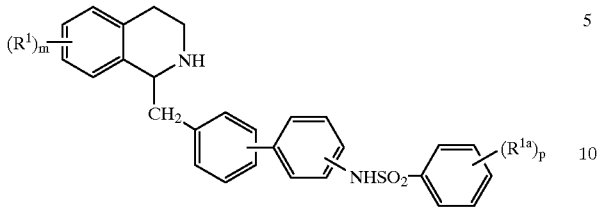

Ia wherein
R¹ is (1) halogen
(2) hydroxy
R$^{1a}$ is (1) Q'COR³
(2) a 5 or 6-membered heterocyclic ring with from 1 to 4 heteroatoms selected from oxygen, sulfur and nitrogen, optionally substituted with up to 5 groups independently selected from
(a) R²,
(b) QR²,
(c) halogen,
(d) cyano, and
(e) oxo;
R² is (1) phenyl, optionally substituted with up to 5 groups selected from
(a) halogen,
(b) cyano,
(c) $C_1$–$C_{10}$ alkoxy, optionally substituted with up to 5 halogens,
(d) $C_1$–$C_{10}$ alkyl optionally substituted with up to 5 halogens,
(2) $C_1$–$C_{10}$ alkyl optionally substituted with up to 5 groups selected from
(a) hydroxy,
(b) halogen,
(c) $CO_2R^4$,
(d) $S(O)_n$—$C_1$–$C_{10}$ alkyl, where n is 0 to 2,
(e) $C_3$–$C_8$ cycloalkyl,
(f) $C_1$–$C_{10}$ alkoxy, and
(g) B, where B is as defined in claim 1, optionally substituted with up to 5 groups selected from halogen, trifluoromethyl, trifluoromethoxy, cyano, $C_1$–$C_{10}$ alkyl and $C_1$–$C_{10}$ alkoxy.

7. A compound of claim 6 wherein
m is 1 or 2;
p is 1;
R¹ is hydroxy;
R$^{1a}$ is Q'COR³, or
a 5 or 6-membered heterocyclic ring with from 1 to 4 heteroatoms selected from oxygen, sulfur and nitrogen, optionally substituted with R².

8. A compound of claim 1 selected from the group consisting of:
1) N-[4-[(6,7-dihydroxy-1,2,3,4-tetrahydro-1-isoquinolinyl)methyl]phenyl]-4-[[(hexylamino)carbonyl]amino]benzenesulfonamide, trifluoroacetate;
2) N-[4-[(6,7-dihydroxy-1,2,3,4-tetrahydro-1-isoquinolinyl)methyl]phenyl]-1-[(4-octyl)-2-thiazolyl]-5-indolinesulfonamide, trifluoroacetate;
3) N-[4-[(6,7-dihydroxy-1,2,3,4-tetrahydro-1-isoquinolinyl)methyl]phenyl]-4-(3-octyl-2-imidazolidinon-1-yl)benzenesulfonamide, trifluoroacetate;
4) N-[4-[(6,7-dihydroxy-1,2,3,4-tetrahydro-1-isoquinolinyl)methyl]phenyl]-4-iodobenzenesulfonamide, trifluoroacetate;
5) N-[4-[(6,7-dihydroxy-1,2,3,4-tetrahydro-1-isoquinolinyl)methyl]phenyl]-4-[6-[4-(trifluoromethyl)phenyl]pyrazin-2-yl]benzenesulfonamide, trifluoroacetate;
6) N-[4'-[(6,7-dihydroxy-1,2,3,4-tetrahydro-1-isoquinolinyl)methyl][1,1'-biphenyl]-3-yl]-4-[[(hexylamino)carbonyl]amino]benzenesulfonamide, trifluoroacetate;
7) N-[3'-[(6,7-dihydroxy-1,2,3,4-tetrahydro-1-isoquinolinyl)methyl][1,1'-biphenyl]-4-yl]-4-[[(hexylamino)carbonyl]amino]benzenesulfonamide, trifluoroacetate;
8) N-[4'-[(6,7-dihydroxy-1,2,3,4-tetrahydro-1-isoquinolinyl)methyl][1,1'-biphenyl]-4-yl]-4-[[(hexylamino)carbonyl]amino]benzenesulfonamide, trifluoroacetate;
9) N-[4'-[(6,7-dihydroxy-1,2,3,4-tetrahydro-1-isoquinolinyl)methyl][1,1'-biphenyl]-4-yl]-4-iodobenzenesulfonamide;
10) N-[4'-[(6,7-dihydroxy-1,2,3,4-tetrahydro-1-isoquinolinyl)methyl][1,1'-biphenyl]-4-yl]-4-[4-[4-(trifluoromethyl) phenyl]thiazol-2-yl]benzenesulfonamide;
11) N-[4'-[(6,7-dihydroxy-1,2,3,4-tetrahydro-1-isoquinolinyl)methyl][1,1'-biphenyl]-4-yl]-3-isoquinolinesulfonamide;
12) N-[4'-[(6,7-dihydroxy-1,2,3,4-tetrahydro-1-isoquinolinyl)methyl][1,1'-biphenyl]-4-yl]-4-(trifluoromethoxy)benzenesulfonamide;
13) N-[4'-[(6,7-dihydroxy-1,2,3,4-tetrahydro-1-isoquinolinyl)methyl][1,1'-biphenyl]-4-yl]-methanesulfonamide;
14) N-[4'-[(6,7-dihydroxy-1,2,3,4-tetrahydro-1-isoquinolinyl)methoxy][1,1'-biphenyl]-4-yl]-4-[[(hexylamino)carbonyl]amino]benzenesulfonamide, trifluoroacetate;
15) N-[4'-[(6,7-dihydroxy-1,2,3,4-tetrahydro-1-isoquinolinyl)methoxy][1,1'-biphenyl]-4-yl]-4-iodobenzenesulfonamide, trifluoroacetate;
16) N-[6-[(6,7-dihydroxy-1,2,3,4-tetrahydro-1-isoquinolinyl)methoxy]naphth-2-yl]-4-[[(hexylamino)carbonyl]amino]benzenesulfonamide, trifluoroacetate;
17) N-[6-[(6,7-dihydroxy-1,2,3,4-tetrahydro-1-isoquinolinyl)methoxy]naphth-2-yl]-4-iodobenzenesulfonamide, trifluoroacetate;
18) N-[4'-[(7-hydroxy-1,2,3,4-tetrahydro-1-isoquinolinyl)methyl][1,1'-biphenyl]-4-yl]-4-[[(hexylamino)carbonyl]amino]benzenesulfonamide, trifluoroacetate; and
19) N-[4'-[(7-hydroxy-1,2,3,4-tetrahydro-1-isoquinolinyl)methyl][1,1'-biphenyl]-4-yl]-4-iodobenzenesulfonamide, trifluoroacetate.

9. A method for the treatment of diabetes which comprises administering to a diabetic patient an effective amount of a compound of claim 1.

10. A method for the treatment of obesity in a mammal which comprises administering to mammal an effective amount of a compound of claim 1.

11. A method for lowering triglyceride levels and cholesterol levels or raising high density lipoprotein levels which comprises administering to a patient needing lower triglyceride and cholesterol levels or higher high density lipoprotein levels an effective amount of a compound of claim 1.

12. A method for decreasing gut motility which comprises administering to a patient in need of decreased gut motility, an effective amount of a compound of claim 1.

13. A method for reducing neurogenic inflammation of airways which comprises administering to a patient in need of reduced neurogenic inflammation, an effective amount of a compound of claim 1.

14. A method for reducing depression which comprises administering to a depressed patient an effective amount of a compound of claim 1.

15. A method for treating gastrointestinal disorders which comprises administering to a patient with gastrointestinal disorders an effective amount of a compound of claim 1.

16. A composition for the treatment of diabetes or obesity or for lowering triglyceride or cholesterol levels or increasing high density lipoprotein levels or for decreasing gut motility or for reducing neurogenic inflammation or for treating depression or for treating gastrointestinal disorders which comprises an inert carrier and an effective amount of a compound of claim 1.

17. A pharmaceutical composition which comprises a compound of claim 1 and a pharmaceutically acceptable carrier.

* * * * *